United States Patent
Aber et al.

(10) Patent No.: US 11,065,437 B2
(45) Date of Patent: Jul. 20, 2021

(54) CARDIAC SUPPORT SYSTEMS AND METHODS FOR CHRONIC USE

(71) Applicant: EVERHEART SYSTEMS INC., Webster, TX (US)

(72) Inventors: Greg S. Aber, Houston, TX (US); Neil H. Akkerman, Houston, TX (US); Randolph K. Armstrong, Houston, TX (US)

(73) Assignee: CORVION, INC., Webster, TX (US)

(*) Notice: Subject to any disclaimer, the term of this patent is extended or adjusted under 35 U.S.C. 154(b) by 0 days.

(21) Appl. No.: 16/659,569

(22) Filed: Oct. 22, 2019

(65) Prior Publication Data

US 2020/0046889 A1    Feb. 13, 2020

Related U.S. Application Data

(60) Division of application No. 14/018,374, filed on Sep. 4, 2013, now Pat. No. 10,449,277, which is a
(Continued)

(51) Int. Cl.
- *A61M 1/10* (2006.01)
- *A61M 60/50* (2021.01)
(Continued)

(52) U.S. Cl.
CPC .......... *A61M 60/50* (2021.01); *A61M 60/871* (2021.01); *H01F 38/14* (2013.01);
(Continued)

(58) Field of Classification Search
CPC .................................. A61M 1/10; A61M 1/12
See application file for complete search history.

(56) References Cited

U.S. PATENT DOCUMENTS

| 4,785,827 A | 11/1988 | Fischer |
|---|---|---|
| 5,290,227 A | 3/1994 | Pasque |

(Continued)

FOREIGN PATENT DOCUMENTS

| CA | 2209179 | 7/1996 |
|---|---|---|
| EP | 0714317 | 6/1996 |

(Continued)

OTHER PUBLICATIONS

Dixon, L.H., "Eddy Current Losses in Transformer Windings and Circuit Wiring," <http://focus.ti.com/lit/ml/slup197/slup197.pdf>.
(Continued)

*Primary Examiner* — Matthew W Schall
(74) *Attorney, Agent, or Firm* — Nathan S. Smith; Mark I. Bentley; Morgan, Lewis & Bockius LLP

(57) ABSTRACT

A high efficiency cardiac support system is suitable for chronic use in treating heart failure, wherein the system includes an implantable rotary blood pump, an implantable power module, a wireless power transfer subsystem, a patient monitor, and a programmer. In a cardiac support system, the cumulative efficiencies of the components of the system are capable of providing therapeutically effective blood flow for a typical day of awake hours using the energy from a single wireless recharge of an implanted rechargeable energy source. Moreover, the implantable rechargeable energy source may be recharged during a normal sleep period of 8 hours or less. The system may provide full or partial cardiac support without the need for external wearable batteries, controllers, or cables.

14 Claims, 20 Drawing Sheets

Related U.S. Application Data continuation of application No. 13/038,875, filed on Mar. 2, 2011, now Pat. No. 8,551,163, which is a continuation-in-part of application No. 12/899,748, filed on Oct. 7, 2010, now Pat. No. 9,227,001.

(60) Provisional application No. 61/421,779, filed on Dec. 10, 2010.

(51) Int. Cl.
| | | |
|---|---|---|
| *H02J 50/12* | (2016.01) | |
| *H02J 7/02* | (2016.01) | |
| *A61M 60/871* | (2021.01) | |
| *H01F 38/14* | (2006.01) | |
| *H02J 5/00* | (2016.01) | |
| *A61M 60/00* | (2021.01) | |
| *A61M 60/122* | (2021.01) | |
| *A61M 60/148* | (2021.01) | |
| *A61M 60/205* | (2021.01) | |

(52) U.S. Cl.
CPC ............ *H02J 5/005* (2013.01); *H02J 7/025* (2013.01); *H02J 50/12* (2016.02); *A61M 60/00* (2021.01); *A61M 60/122* (2021.01); *A61M 60/148* (2021.01); *A61M 60/205* (2021.01); *A61M 2205/8243* (2013.01)

(56) References Cited

U.S. PATENT DOCUMENTS

| | | |
|---|---|---|
| 5,370,509 A | 12/1994 | Golding et al. |
| 5,702,431 A | 12/1997 | Wang et al. |
| 6,048,363 A | 4/2000 | Nagyszalanczy et al. |
| 6,227,797 B1 | 5/2001 | Watterson et al. |
| 6,234,772 B1 | 5/2001 | Wampler et al. |
| 6,240,318 B1 | 5/2001 | Phillips |
| 6,445,956 B1 | 9/2002 | Laird et al. |
| 6,547,530 B2 | 4/2003 | Ozaki et al. |
| 6,593,841 B1 | 7/2003 | Mizoguchi et al. |
| 6,894,456 B2 | 5/2005 | Tsukamoto et al. |
| 7,616,997 B2 | 11/2009 | Kieval et al. |
| 7,682,301 B2 | 3/2010 | Wampler et al. |
| 7,699,586 B2 | 4/2010 | LaRose et al. |
| 7,741,734 B2 | 6/2010 | Joannopoulos |
| 7,825,543 B2 | 11/2010 | Karalis et al. |
| 8,362,651 B2 | 1/2013 | Hamam et al. |
| 8,551,163 B2 | 10/2013 | Aber |
| 8,901,775 B2 | 12/2014 | Armstrong |
| 2003/0091249 A1 | 5/2003 | Kurimura et al. |
| 2006/0155159 A1 | 7/2006 | Melvin |
| 2008/0211320 A1 | 9/2008 | Cook et al. |
| 2008/0269828 A1 | 10/2008 | Sequeira Abreu |
| 2009/0051224 A1 | 2/2009 | Cook et al. |
| 2009/0058189 A1 | 3/2009 | Cook et al. |
| 2009/0058361 A1 | 3/2009 | John |
| 2009/0072628 A1 | 3/2009 | Cook et al. |
| 2009/0079268 A1 | 3/2009 | Cook et al. |
| 2009/0112626 A1 | 4/2009 | Talbot et al. |
| 2009/0171420 A1 | 7/2009 | Brown et al. |
| 2009/0224609 A1 | 9/2009 | Cook et al. |
| 2009/0234447 A1 | 9/2009 | LaRose et al. |
| 2009/0270679 A1 | 10/2009 | Hoeg et al. |
| 2010/0045114 A1 | 2/2010 | Sample et al. |
| 2010/0052811 A1 | 3/2010 | Smith et al. |
| 2010/0060431 A1 | 3/2010 | Stevenson et al. |
| 2010/0063347 A1 | 3/2010 | Yomtov et al. |
| 2010/0102640 A1 | 4/2010 | Joannopoulos et al. |
| 2010/0102641 A1 | 4/2010 | Joannopoulos et al. |
| 2010/0109445 A1 | 5/2010 | Kurs et al. |
| 2010/0117456 A1 | 5/2010 | Karalis et al. |
| 2010/0133920 A1 | 6/2010 | Joannopoulos et al. |
| 2010/0164296 A1 | 7/2010 | Kurs et al. |
| 2010/0184371 A1 | 7/2010 | Cook et al. |
| 2010/0185280 A1 | 7/2010 | Ayre et al. |
| 2010/0210233 A1 | 8/2010 | Cook et al. |
| 2010/0219694 A1 | 9/2010 | Kurs et al. |
| 2010/0231053 A1 | 9/2010 | Karalis et al. |
| 2010/0259108 A1 | 10/2010 | Giler et al. |
| 2010/0277005 A1 | 11/2010 | Karalis et al. |
| 2010/0305662 A1 | 12/2010 | Ozawa et al. |
| 2010/0327661 A1 | 12/2010 | Karalis et al. |
| 2011/0195666 A1 | 8/2011 | Forsell |
| 2011/0281535 A1 | 11/2011 | Low et al. |
| 2012/0010079 A1 | 1/2012 | Sedwick |
| 2012/0032522 A1 | 2/2012 | Schatz et al. |
| 2012/0089225 A1 | 4/2012 | Akkerman |
| 2012/0112554 A1 | 5/2012 | Kim et al. |
| 2012/0119587 A1 | 5/2012 | Cheon et al. |
| 2012/0139355 A1 | 6/2012 | Ganem et al. |
| 2012/0146575 A1 | 6/2012 | Armstrong et al. |
| 2012/0150291 A1 | 6/2012 | Aber et al. |
| 2012/0153893 A1 | 6/2012 | Schatz et al. |
| 2013/0241306 A1 | 9/2013 | Aber |
| 2014/0252873 A1 | 9/2014 | Irish |
| 2014/0255225 A1 | 9/2014 | Aber |
| 2015/0061591 A1 | 3/2015 | Armstrong |

FOREIGN PATENT DOCUMENTS

| | | |
|---|---|---|
| EP | 1113177 | 7/2001 |
| WO | WO 2009/091267 | 7/2009 |
| WO | WO 2010/042054 | 4/2010 |

OTHER PUBLICATIONS

Murgatroyd, et al., "The Frequency Dependence of Resistance in Foilwound Inductors," Electrocomponent Science and Technology 1979, vol. 5, pp. 219-222.

Sample, et al., "Analysis, Experimental Results, and Range Adaptation of Magnetically Coupled Resonators for Wireless Power Transfer," IEEE, 2010.

Kurs, A., "Power Transfer Through Strongly Coupled Resonances," MIT Department of Physics, Master's Thesis, Sep. 2007.

Extended European Search Report from European Patent Application No. 17159937.6, dated Jul. 4, 2017.

European Office Action dated Nov. 7, 2016, which issued European Application No. 14159404.4.

(SECTION A - A)

(SECTION B - B)

(DETAIL C)

(DETAIL D)

CONVEX

CONCAVE

CONVEX

CONCAVE (DETAIL E)

(Section G-G)

(DETAIL H)

CARDIAC SUPPORT SYSTEMS AND METHODS FOR CHRONIC USE

RELATED APPLICATIONS

This application is a divisional of U.S. application Ser. No. 14/018,374 filed Sep. 4, 2013, which is a continuation of U.S. application Ser. No. 13/038,875 filed Mar. 2, 2011, now U.S. Pat. No. 8,551,163, which (a) is a continuation-in-part of U.S. application Ser. No. 12/899,748 filed Oct. 7, 2010, now U.S. Pat. No. 9,227,001, and (b) claims benefit to priority to U.S. Application Ser. No. 61/421,779 filed Dec. 10, 2010, which are incorporated herein in their entirety by reference.

FIELD OF THE INVENTION

This invention relates to implantable cardiac support systems, particularly implantable blood pump systems for the treatment of heart failure.

BACKGROUND OF INVENTION

In patients with heart failure, there is a need for therapeutically enhancing blood flow using an implantable system. Cardiac support systems include, but are not limited to, left ventricular assist devices (LVADs), right ventricular assist devices (RVADs), using two devices to assist both ventricles as a bi-ventricular assist device (BiVADs), and total artificial hearts (TAHs). Ventricular assist devices (VADs) that are suitable for adults may call for approximately 5 liters/min (LPM) of blood flow at 100 mm of Hg differential pressure which equates to about 1 watt of hydraulic power. Currently available implantable continuous flow blood pumps consume significantly more electric power to produce the desired amount of flow and pressure.

High pump power consumption of current systems may make it impractical to implant a power source of sufficient capacity for a full day of awake hours of operation in the body. For example, size restrictions of implantable power sources may only allow the implantable power source to provide up to an hour of operation time. Instead, high power consumption blood pumps may provide a wire connected to the pump that exits the body (i.e. percutaneous) for connection to a power source that is significantly larger than an implantable power source. These blood pumps may require external power to be provided at all times to operate. In order to provide some mobility, external bulky batteries and controllers may be utilized. However, percutaneous wires and externally worn components can still restrict the mobility of a person with such a blood pump implant. For example, such high power consumption blood pumps have external batteries that frequently require recharging thereby limiting the amount of time the person can be away from a charger or power source, external batteries and controllers that can be heavy or burdensome thereby restricting mobility, percutaneous wire skin penetrations that are not suitable for prolonged exposure to water submersion (i.e. swimming, bathing, etc.), and/or other additional drawbacks.

For example, negative impacts of these types of systems may include susceptibility to infection, constraints on sleep position, restrictions on water activities such as swimming and bathing, concern for wire entanglement or severing, necessity to avoid static discharges, and a multitude of others. Furthermore, the external batteries and control systems are burdensome. It would be advantageous to eliminate the percutaneous wire and burdensome external batteries and control system.

While there is limited use of wireless power systems in some neural stimulators, widespread use of wireless power systems for implantable heart pumps has not been adopted. Currently, few applications of wireless power transfer have been applied to VADs or TAHs due to the higher power transfer levels required, relatively high power consumption of such devices, limited space available for implantable rechargeable batteries, limited capacity of implantable rechargeable batteries, and the like.

However, in order to overcome issues associated with percutaneous wires, some wireless power transfer systems have been developed that use inductive coupling between an implanted coil and an external coil to transfer power across the skin, thereby obviating the need for a percutaneous wire. This type of wireless power transfer system simply uses the inductive effect between two coils similar to a standard transformer. This approach has been used widely to recharge implanted batteries in some neural stimulators. Further, these inductive systems may require precise alignment between the two coils, and may require close spacing between coils on the order of a few inches or less. These inductive systems can generate significant amounts of heat near the skin, and require the patient to be immobile during charging if the external power source is not easily mobile. Energy lost by such systems is generally released as heat that is dissipated into the human body, which may produce heat-related health complications or require additional components to compensate for the heat generated.

LionHeart LVD-2000™ LVAD from Arrow International, Inc. and the HeartSaver™ LVAD from WorldHeart Corporation eliminated the percutaneous wire by powering the implanted portion using inductively-coupled Transcutaneous Energy Transfer (TET). These systems eliminated the wire, but did not eliminate the burdensome external batteries and control system which still had to be worn by the patient. For example, the LionHeart LVD-2000 had a rechargeable implantable battery for brief periods when the external power was unavailable or needed to be removed. However, due to the energy demands of the implanted system, that implantable battery could supply only about 20 minutes of energy. Note that the size of an acceptable system for implanting into a patient constrains the capacity of implantable energy storage. Consequently, although the LionHeart LVD-2000 did not require a percutaneous wire, the burden of the external batteries and controller remained similar to that of systems with a percutaneous wire.

Implantable cardiac support systems have numerous sources of potential energy inefficiency. To produce a therapeutically enhanced blood flow, power is needed to produce a particular desired blood flow rate at a particular desired pressure. Blood flow may be imparted by an electro-mechanical device, such as by a rotary pump. The design of the electro-mechanical device is critical to efficiently transferring the electrical energy powering the device into the desired blood flow. Further, a cardiac support system may also include an energy storage system. The design and operation of the energy storage system is critical to efficiently maintain and transfer stored electrical energy.

As a result of the significant drawbacks of existing systems, there is an unmet need for an energy-efficient cardiac support system capable of eliminating percutaneous wires for power or control, and doing so without burdening the patient with external batteries or controllers. There is an unmet need for a system which not only restores cardiac function, but restores an unburdened ambulatory lifestyle.

SUMMARY OF THE INVENTION

In an illustrative implementation, a cardiac support system includes a rotary blood pump that is implantable into the human body, wherein the rotary blood pump generates a desired amount of blood flow; and a power module connected to the rotary blood pump, wherein the power module stores electrical energy utilized to operate the rotary blood pump, and the power module is implantable into the human body. The system further includes a receiving coil assembly coupled to the power module, wherein the receiving coil assembly is implantable into the human body, and a transmitting coil assembly magnetic resonance coupled to the receiving coil assembly, wherein the transmitting coil assembly is utilized to electromagnetically transfer energy to the receiving coil assembly.

In another illustrative implementation, a method for providing cardiac support to a patient includes generating a desired amount of blood flow with a rotary blood pump implanted in the patient; storing electrical energy in a power module implanted in the patient, wherein the power module stores electrical energy received from a receiving coil assembly implanted in the patient; and coupling a transmitting coil assembly to the receiving coil assembly using magnetic resonance coupling, wherein the transmitting coil assembly electromagnetically transfers energy to the receiving coil assembly.

In yet another illustrative implementation, a cardiac support system includes a rotary blood pump that is implantable into the human body, wherein said rotary blood pump generates a desired amount of blood flow, and a power module connected to said rotary blood pump, wherein said power module is implantable into said human body. The system also includes a receiving coil assembly receiving energy wirelessly, wherein said receiving coil assembly is implantable into said human body, said receiving coil assembly transfers said energy into said power module, and said desired amount of blood flow is generated with an Energy Conversion Ratio (ECR) of 1.0 or greater using energy stored by said power module. The ECR is defined as the sustained flow rate (in LPM) a cardiac support system can provide against 100 mm-Hg differential pressure for 24 hours from a 40 Watt-hour rechargeable energy source.

In yet another illustrative implementation, a method for treating heart failure is disclosed. The method includes receiving energy wirelessly via a receiving coil assembly, wherein said receiving coil assembly is implantable into the human body, and storing said energy in a power module, wherein said power module is implantable into said human body. The method also includes producing a desired amount of blood flow from a rotary blood pump utilizing energy provided by said power module, wherein said rotary blood pump is implantable into said human body, and said desired amount of blood flow is generated with an Energy Conversion Ratio (ECR) of 1.0 or greater using energy stored by said power module.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific implementations of the disclosure, wherein:

FIG. 10A-10D are cross-sectional views of various shapes of pattern grooves;

DETAILED DESCRIPTION

Figure 1:
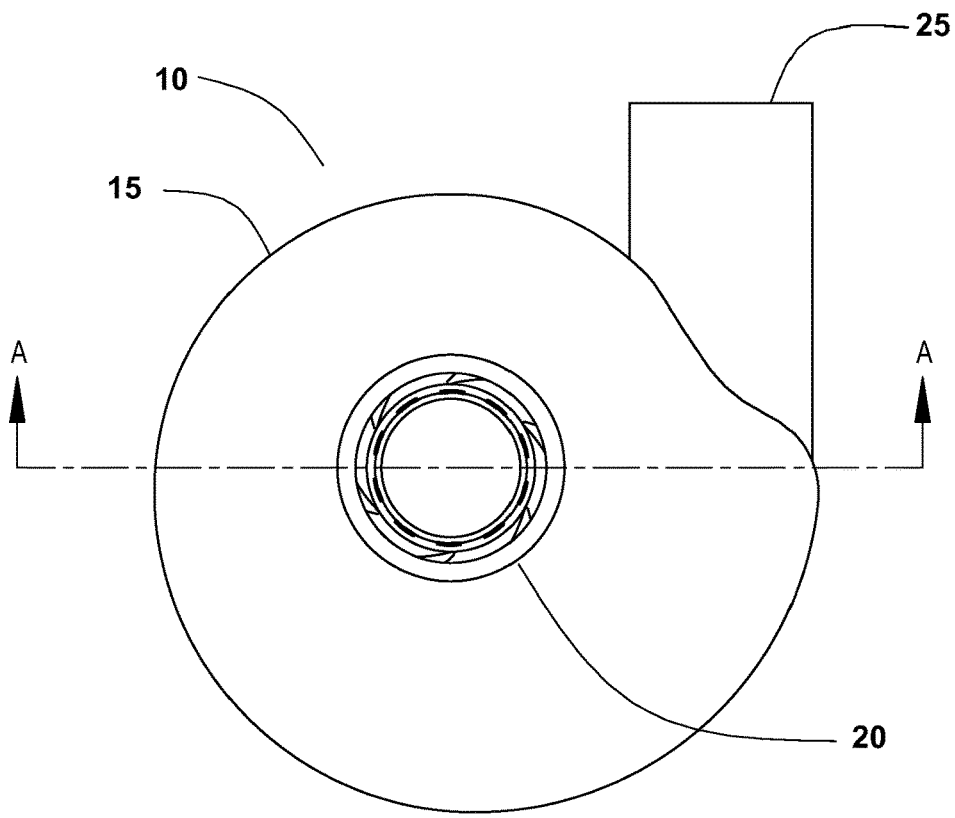
FIG. 1 is a top view of an illustrative implementation of a rotary blood pump.

Refer now to the drawings wherein depicted elements are not necessarily shown to scale and wherein like or similar elements may be designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

The following detailed description provides for an implantable, energy efficient, small, and wireless cardiac support system. The cardiac support system may include an implantable rotary blood pump, an implantable power module, and a wireless power transfer subsystem. The implantable rotary blood pump may be powered by an implantable power module which can be recharged using a wireless power transfer subsystem. Those skilled in the art will appreciate that the various features discussed below can be combined in various manners, in addition to the implementations discussed below. The scope of the claims is in no way limited to the specific implementations discussed herein.

In response to unmet needs, the cardiac support system may use a power-efficient rotary blood pump, an efficient power module, and a wireless power subsystem, and/or other components, as discussed further herein. Currently available cardiac support systems may have several drawbacks, such as percutaneous wire(s), bulky external battery packs and controllers, and/or required frequent and close distance recharging. The cardiac support system discussed herein is capable of providing the enhanced blood flow needed by an average patient during a typical day of awake hours utilizing power stored by an implanted energy storage device. The implanted energy storage device is capable of being wirelessly recharged over a significant charging distance during a typical sleep period of 8 hours or less. The cardiac support system may also include external monitoring devices useful to notify the patient and/or other caregivers of system status and/or other issues.

Implantable Rotary Blood Pump

An implantable rotary blood pump may assist or fully support the required blood flow of a patient. For example, implantable rotary blood pumps may have circulatory assist uses including, but not limited to, ventricular assist (right, left and both) and heart replacement. For the purpose of illustration, a highly efficient blood pump is discussed below. However, it should be noted that an implantable rotary blood pump is in no way limited to the specific implementations discussed below. FIG. 1 is a top view of an illustrative implementation of an implantable rotary blood pump 10 hereinafter referred to as pump 10. Pump 10 is formed from pump housing 15 providing inlet 20 and outlet 25 and motor housing 35. Pump housing 15 is composed of two or more pieces and may be joined by welding. However, in other implementations, pump housing 15 may be joined by fusing, press fit, threading, screw and elastomeric sealing, bonding, fasteners, and/or any other suitable joining method or combinations of joining methods. Motor housing 35 may be joined to pump housing 15 by welding, fusing, press fit, threading, screw and elastomeric sealing, bonding, fasteners, and/or any other suitable joining method or combinations of joining methods. Line A-A passing through pump housing 15 indicates the plane from which the cross-sectional view in FIG. 2 is provided.

Figure 2:
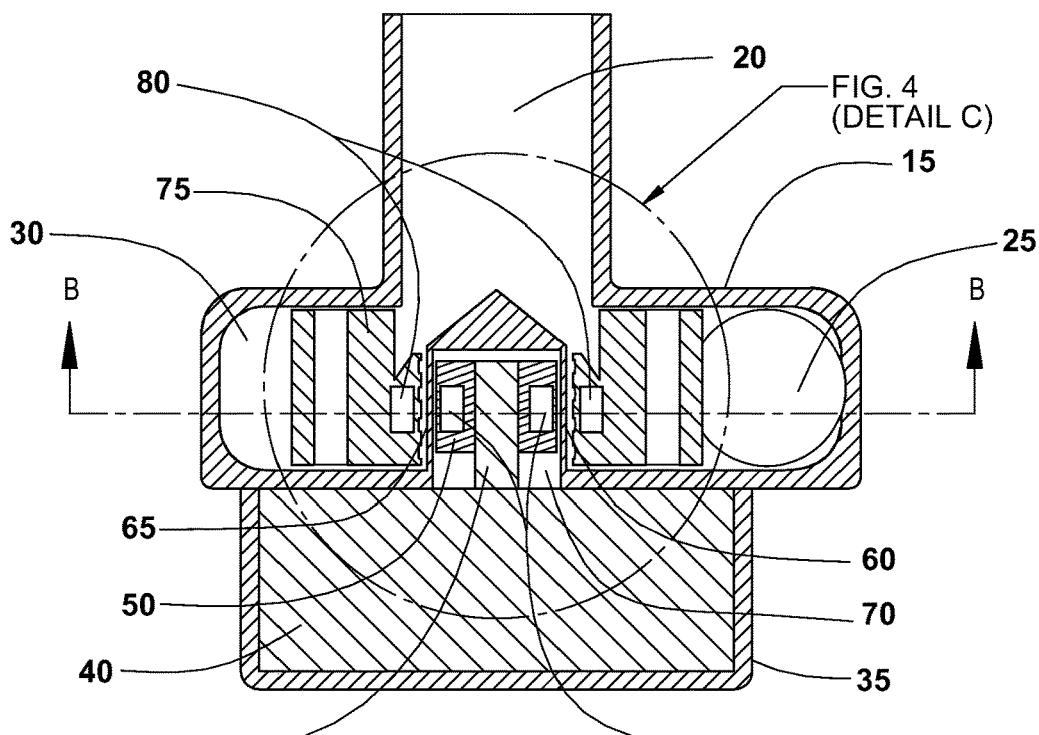
FIG. 2 is a cross-sectional side view of an illustrative implementation of a rotary blood pump.

FIG. 2 is a cross-sectional side view of an illustrative implementation of pump 10. Pump housing 15 provides impeller chamber 30 for impeller 75. Impeller chamber 30 has inlet 20 for connection to a fluid source and outlet 25 for providing fluid to a desired location. Impeller chamber 30 is sealed and pressure tight to prevent fluid from entering/exiting impeller chamber 30 from locations other than inlet 20 and outlet 25.

Figure 7:
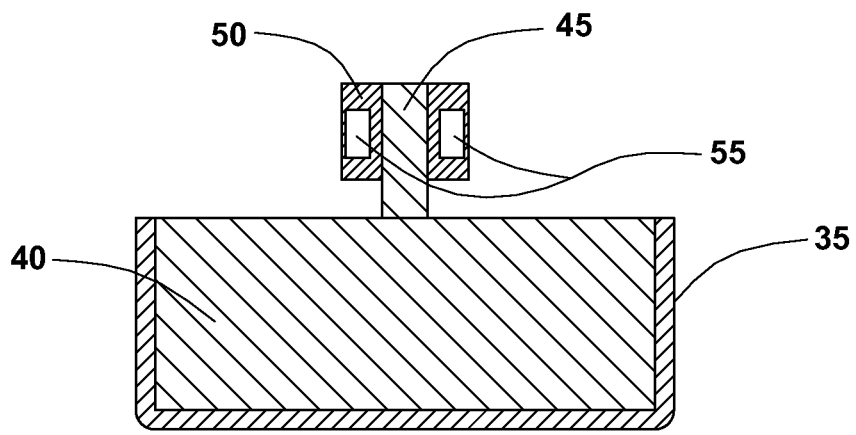
FIG. 7 is a cross-sectional view of an illustrative implementation of a motor housing for use in a rotary blood pump.

Motor housing 35 is attached to pump housing 15 to form a fluid and/or pressure tight chamber for motor 40. While motor housing 35 is shown as a separate component from pump housing 15, in other implementations, pump housing 15 and motor housing 35 may be combined to form a single combined housing. A cross-sectional view of an illustrative implementation of motor 40 and motor housing 35 of pump 10 is shown in FIG. 7. In particular, motor housing 35 is shown separate from pump 10. Motor 40 is entirely contained between pump housing 15 and motor housing 35. A high efficiency electric motor can be utilized, such as an electric motor with efficiency of about 85% or greater. However, in other implementations, any other suitable driving means can be utilized. Motor 40 provides shaft 45 with hub 50 mounted to shaft 45. Hub 50 contains one or more permanent magnets and/or magnetic materials 55. Motor 40 rotates shaft 50 causing permanent magnets 55 placed in hub 50 to rotate. In some implementations, a motor with a useful life of greater than 10 years is utilized. Further, the motor may utilize hydrodynamic bearings with fluid support provided by a fluid other than blood.

Figure 6:
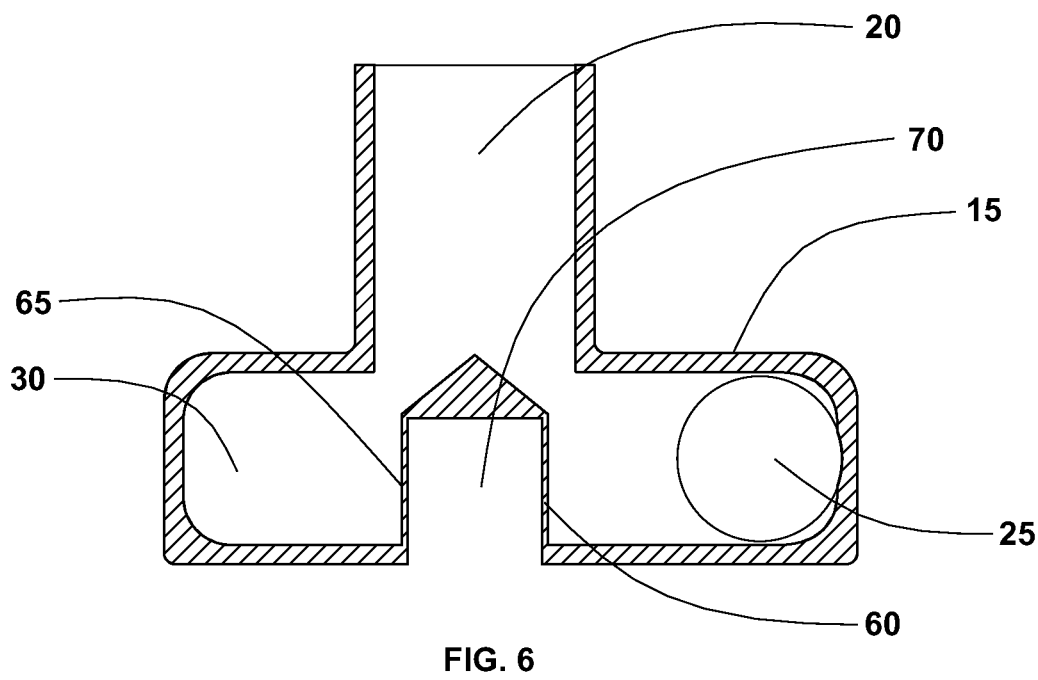
FIG. 6 is a cross-sectional view of an illustrative implementation of a rotary blood pump housing.

A cross-sectional view of an illustrative implementation of pump housing 15 without impeller 75 is shown in FIG. 6. Pump housing 15 may provide a non-ferromagnetic and/or non-electrically conductive diaphragm 60 separating impeller chamber 30 from the chamber housing motor 40. Diaphragm 60 defines cavity 70 providing a region for hub 50 to rotate within. Additionally, diaphragm 60 may provide cylindrical bearing surface 65 for impeller 75 to rotate around with hydrodynamic radial support. Impeller 75 includes one or more permanent magnets and/or magnetic materials 80. Permanent magnets 80 allow impeller 75 to be magnetically coupled to hub 50. This magnetic coupling allows motor 40 to cause impeller 75 to rotate when motor 40 rotates hub 50.

Figure 3:
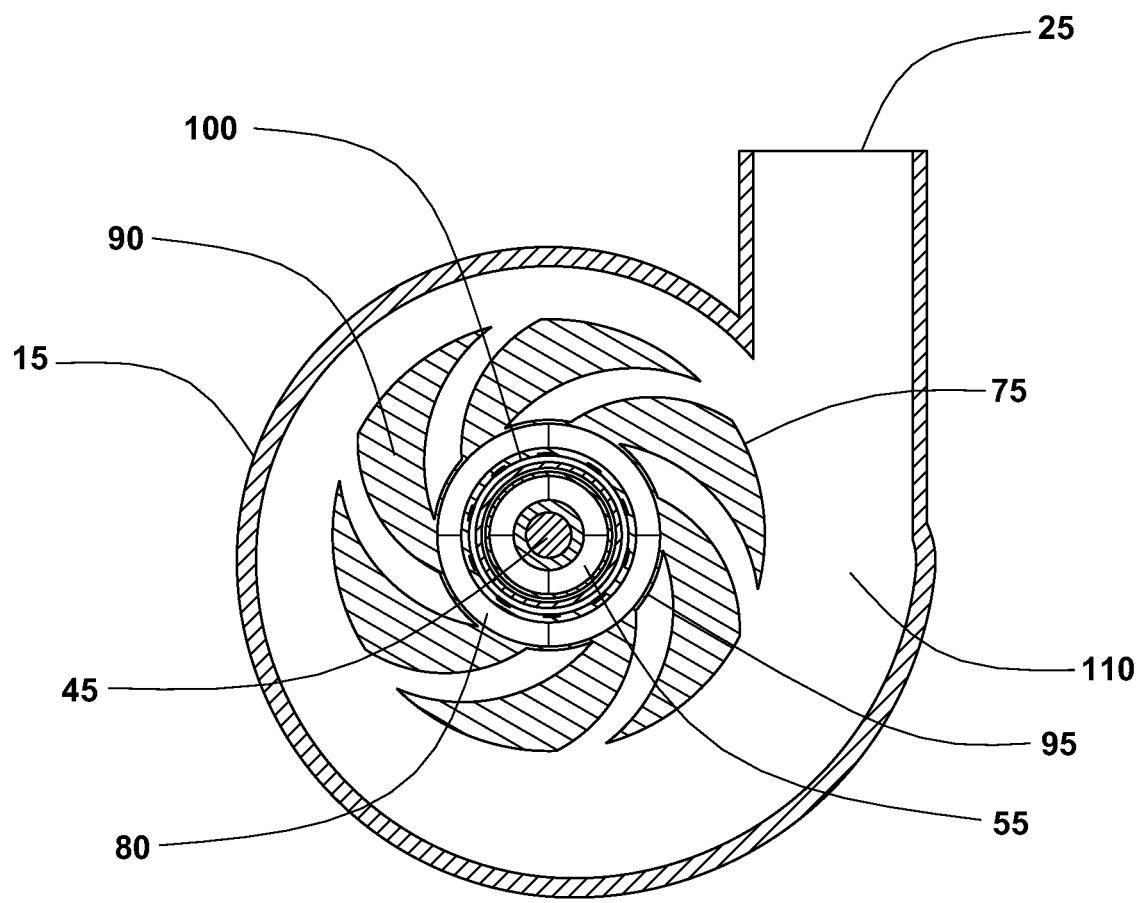
FIG. 3 is a cross-sectional top view of an illustrative implementation of a rotary blood pump.

Line B-B passing through pump housing 15 indicates the plane from which the cross-section view in FIG. 3 is provided. FIG. 3 is a cross-sectional top view of an illustrative implementation of pump 10. Impeller 75 is composed of an array of arc shaped segments 90 joined by central ring 95. Pump housing 15 has volute 110 feeding the outlet 25. In other implementations, volute 110 could be omitted from pump housing 15 and outlet 25 could have any suitable orientation and shape. Pump housing 15 is designed in a manner where impeller 75, when rotated, pressures and moves fluid received from inlet 20 to outlet 25.

Permanent magnets 55 in hub 50 and permanent magnets 80 in central ring 95 of impeller 75 form a magnetic coupling between the impeller 75 and hub 50. In contrast to radial magnetic bearings that are arranged to repel each other, permanent magnets 55 and 80 are arranged so that they are attracted to each other. In order to minimize radial loads, permanent magnets 55 and 80 provide a minimal magnetic coupling or just enough of a magnetic coupling to rotate impeller 75 under load. The attractive force of the magnetic coupling of permanent magnets 55 and 80 also provides axial restraint of impeller 75. For example, axial movement of impeller 75 would misalign permanent magnets 55 and 80. The magnetic forces of permanent magnets 55 and 80 would restrain and re-align the magnets. Because of the magnetic forces caused by permanent magnets 55 and 80, axial movement of impeller 75 may cause axial force to be exerted on shaft 45 and hub 50 of motor 40, which is then transferred to bearing(s) (not shown) of motor 40.

Permanent magnets 80 may be sufficiently small in size that they have no impact on the main fluid flow paths of impeller 75, thereby allowing the design of impeller 75 to focus on fully optimizing pump efficiency. These benefits can allow pumping efficiencies of greater than 50% to be achieved.

Figure 5:
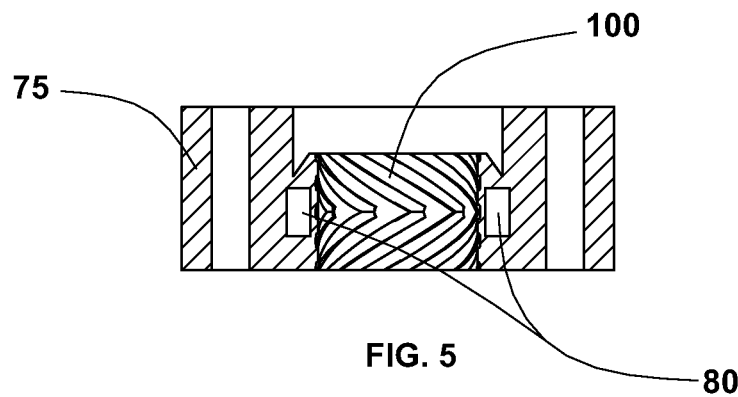
FIG. 5 is a cross-sectional view of an illustrative implementation of an impeller for use in a rotary blood pump.
Figure 8:
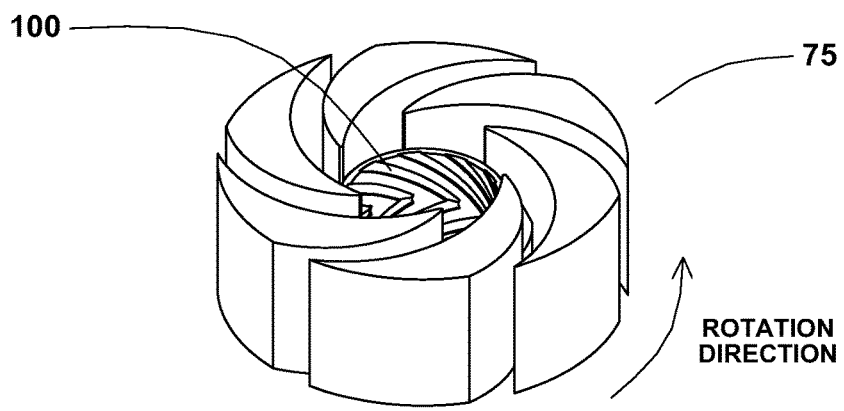
FIG. 8 is an isometric view of an illustrative implementation of an impeller for use in a rotary blood pump.

Impeller internal surface 100 of central ring 95 is utilized to form a hydrodynamic bearing between cylindrical bearing surface 65 and impeller internal surface 100. Impeller 75 is configured to rotate within impeller chamber 30 with full radial hydrodynamic support from the hydrodynamic bearing formed by cylindrical bearing surface 65 and impeller internal surface 100. A cross section view of an illustrative implementation of impeller 75 is shown in FIG. 5 and an isometric view of an illustrative implementation of impeller 75 is shown in FIG. 8, which more thoroughly illustrate the hydrodynamic bearing.

Pattern grooves on impeller internal surface 100 of impeller 75 create a high pressure zone when impeller 75 is rotated, thereby creating a hydrodynamic bearing. For example, symmetrical herringbone grooves create a high pressure zone where the two straight lines of the V-shape grooves meet or the central portion of the symmetrical herringbone grooves. The pressure created by the pattern grooves on impeller internal surface 100 acts as a radial stabilizing force for impeller 75 when it is rotating concentrically. While the implementation shown provides symmetrical herringbone grooves on internal surface 100 of impeller 75, a variety of different groove patterns may be utilized on impeller internal surface 100 to provide a hydrodynamic bearing, which is discussed in detail below. Because low loads are exerted on impeller 75, the radial hydrodynamic bearing formed between cylindrical bearing surface 65 and impeller internal surface 100 can provide stable radial support of impeller 75.

Impeller 75 may be an open, pressure balanced type impeller to minimize axial thrust. Impeller 75 is considered to be open because there is no endplate on either side of arc shaped segments 90. Further, impeller 75 is considered to be pressure balanced because it is designed to minimize axial thrust during the rotation of impeller 75. However, other types of impellers may be suitable in other implementations. Impeller 75 could be any other suitable blade shape, rotate in the opposite direction, or non-pressure balanced. For example, other suitable impellers may be semi-open type (i.e. end plate on one side of impeller) or closed type (i.e. end plate on both sides of impeller).

Figure 4:
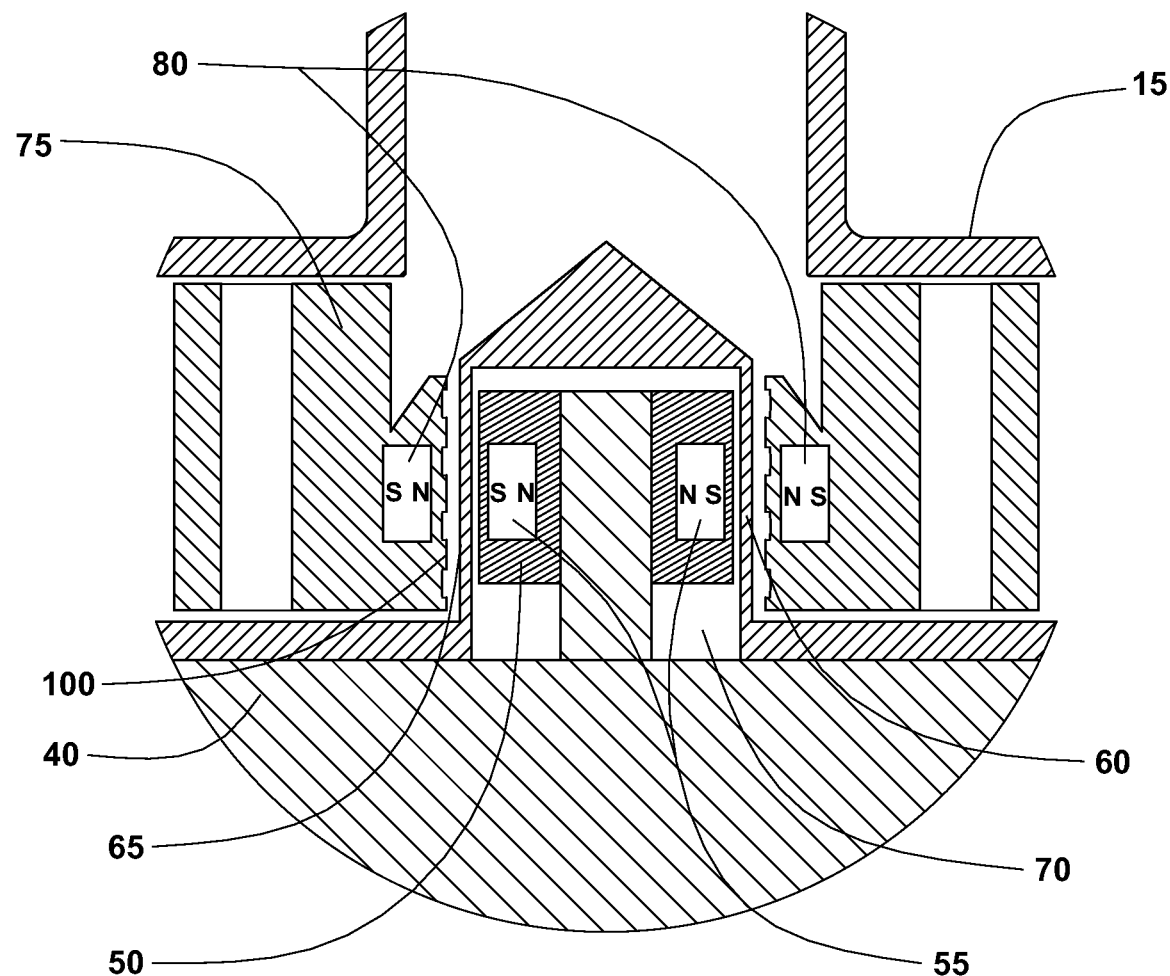
FIG. 4 is a close up cross-sectional view of an area of an illustrative implementation of a rotary blood pump.

FIG. 4 is a close up cross-sectional view of an area C (see FIG. 2) of an illustrative implementation of pump 10. The magnetic coupling transmits torque from shaft 45 of the motor 40 to impeller 75. In the implementation shown, permanent magnets 55 and 80 are radially distributed around hub 50 and impeller 75. The poles of permanent magnets 55 and 80 are arranged to attract each other. The attractive force of the magnetic coupling of permanent magnets 55 and 80 provides axial restraint of impeller 75. While permanent magnets 55 and 80 are shown as arc shaped like quadrants of a cylinder, it should be recognized that permanent magnets 55 and 80 may be shaped in a variety of different manners to provide the magnetic coupling. For example, one or more ring shaped magnets polarized with arc shaped magnetic regions, square/rectangular shaped, rod shaped, disc shaped, or the like may be utilized. In the magnetic coupling arrangement shown, permanent magnets 80 are shown in the internal portion of impeller 75. Internal magnetic couplings, similar to the arrangement shown, can be more efficient than face or external type magnetic couplings that place the magnets in the blades of an impeller or rotor because they have a smaller diameter and less eddy current losses. Diaphragm 60, intermediate the coupling, is non-ferromagnetic and/or non-electrically conductive to minimize eddy current losses. For example, couplings with non-electrically conducting diaphragms such as bio-compatible ceramic, glass or the like, would exhibit less eddy current losses than those with electrically conducting diaphragms.

In one implementation, motor 40 is of the brushless DC, sensorless, iron core type electric motor with fluid dynamic bearings. However, in other implementations, any suitable type of motor including one or more features such as, but not limited to, brushed, hall-effect sensored, coreless, and Halbach array or any type of bearing such as ball or bushing may be used. Motor housing 35 may include motor control circuitry or be configured to operate with remotely located control circuits.

Separating motor 40 from impeller chamber 30 may allow a high efficiency motor to be utilized. For example, incorporating components into a pump impeller to form the rotor of an electric motor may compromise the design of the pump impeller resulting in reduced efficiency. Further, designing a rotor and stator that is incorporated into the design of a pump may result in an electric motor with large gaps between components of the rotor and stator, thereby decreasing the efficiency of the motor. The magnetic coupling arrangements utilized in the implementations discussed herein allow a highly efficient motor design to be utilized without compromising the design of an efficient pump impeller.

Figure 9A:
FIG. 9A-9K are illustrative implementations of various types of pattern grooves.
Figure 10A:
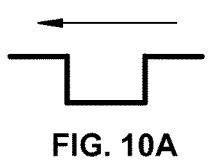
Figure 9B:
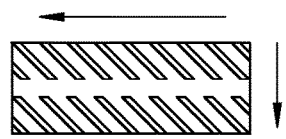
Figure 9C:
Figure 10B:
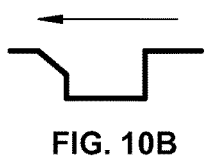
Figure 9D:
Figure 9E:
Figure 10C:
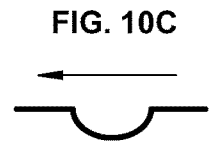
Figure 9F:
Figure 9G:
Figure 9H:
Figure 9I:
Figure 9J:
Figure 9K:
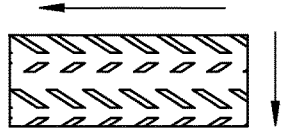

FIGS. 9A-9K and 10A-10D illustrate various implementations of pattern grooves that may be implemented on impeller internal surface 100. As discussed previously, impeller internal surface 100 provides a hydrodynamic journal bearing. For example, impeller internal surface 100 may utilize patterned grooves. The pattern grooves may be of any type including, but not limited to, half herringbone (FIG. 9A), dual half herringbone (FIG. 9B), symmetrical herringbone (FIG. 9C), dual symmetrical herringbone (FIG. 9D), open symmetrical herringbone (FIG. 9E), open dual symmetrical herringbone (FIG. 9F), asymmetrical herringbone (FIG. 9G), continuous asymmetrical dual herringbone (FIG. 9H), asymmetrical dual herringbone (FIG. 9I), asymmetrical open herringbone (FIG. 9J), asymmetrical open dual herringbone (FIG. 9K), or the like. Flow inducing pattern grooves, such as half herringbone patterns and asymmetrical herringbone patterns, have the added benefit of producing a substantial secondary flow, particularly along the axis of impeller rotation between cylindrical bearing surface 65 and impeller 75, thereby minimizing stagnant flow between cylindrical bearing surface 65 and impeller 75. Because stagnant areas may cause blood clots to form in blood pumps, the secondary flow reduces the chances of blood clots forming. Further, asymmetrical herringbone patterns have the additional benefit over half herringbone patterns in that they provide similar radial stiffness as symmetrical herringbone patterns. As shown in FIG. 10A-10D, each of the pattern grooves of internal surface 100 can be shaped in a variety of different manners, such as, but not limited to, rectangular grooves, rectangular grooves with a bevel, semi-circular grooves, elliptical grooves, or the like. In other implementations, impeller internal surface 100 may also be a plain journal bearing without pattern grooves or a multi-lobe shape that creates a hydrodynamic bearing. In alternative implementations, the pattern grooves or multi-lobe shapes may be located on the surface of cylindrical bearing surface 65 facing impeller 75 rather than impeller internal surface 100 or the pattern grooves may be located on an outer radial surface of impeller 75 or internal radial surface of pump housing 15 facing the impeller 75.

Figure 11:
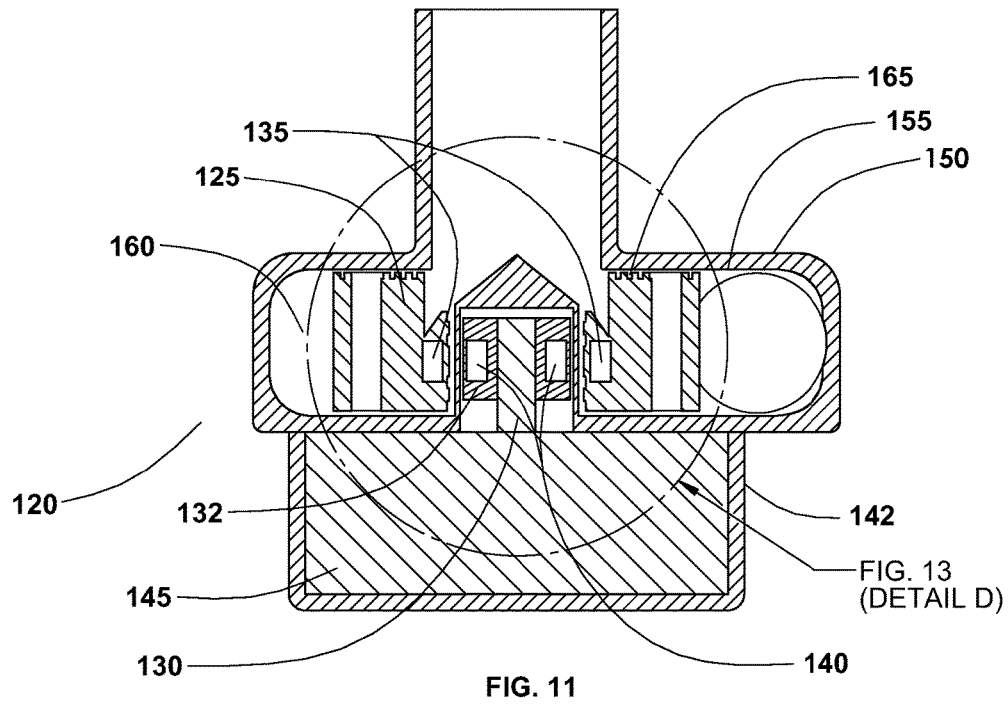
FIG. 11 is a cross-sectional side view of an illustrative implementation of a rotary blood pump with an axial hydrodynamic bearing.

FIG. 11 provides a cross-sectional side view of an illustrative implementation of housing 150 for pump 120. Similar to the implementation shown in FIG. 2, pump 120 provides pump housing 150, impeller 125, shaft 130, hub 132, permanent magnets 135 and 140, motor housing 142, motor 145, and impeller chamber 160, which all provide a similar function to the components discussed previously. These common elements may operate in substantially the same manner as previously described. The substantial differences in the implementations are discussed below.

The implementation shown in FIG. 2 provided radial support of impeller 75 utilizing a hydrodynamic bearing. However in FIG. 11, in addition to a radial hydrodynamic bearing, one or more external planar surfaces or top surfaces 165 of impeller 125 include pattern grooves providing partial axial hydrodynamic support.

Figure 13:
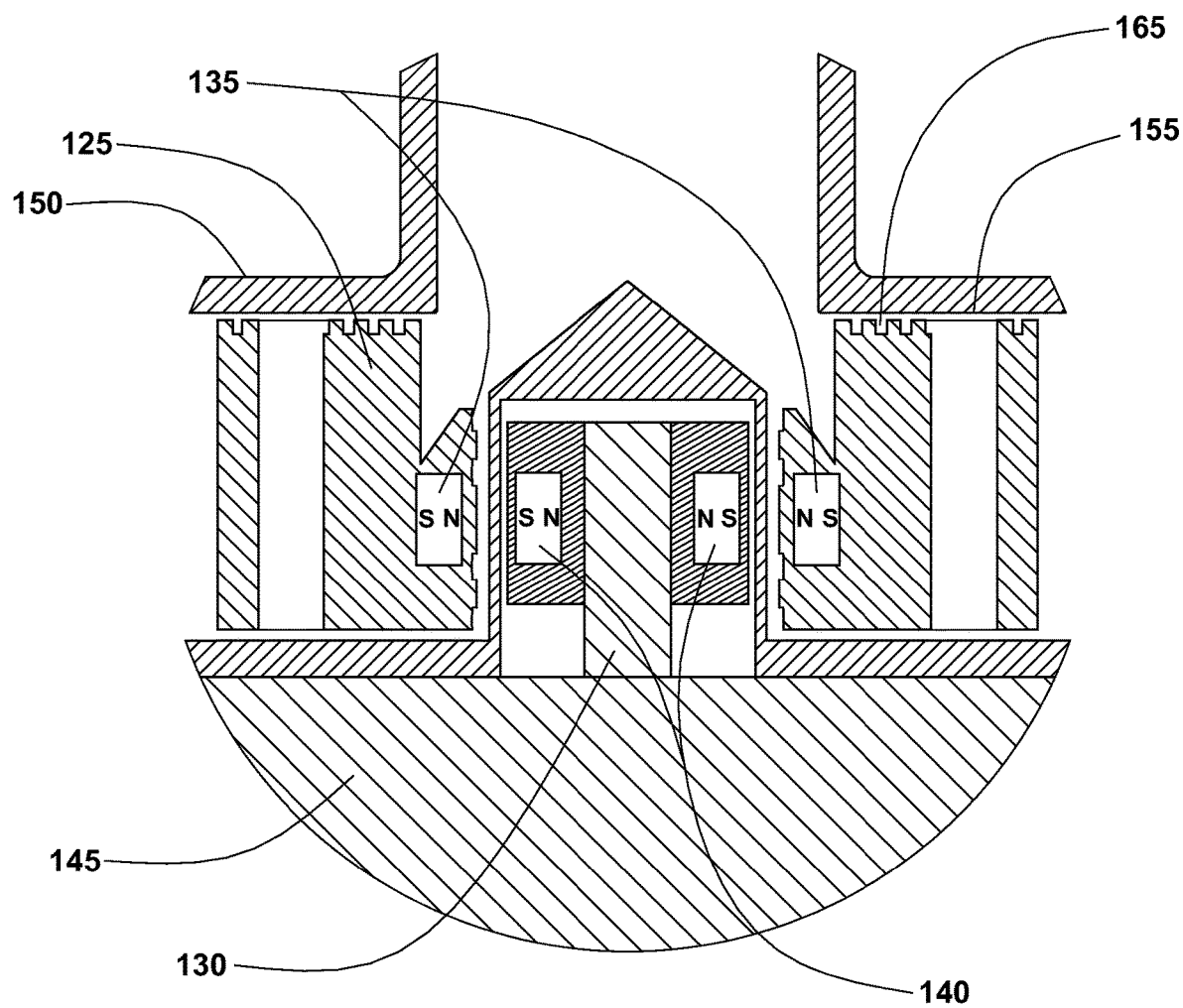
FIG. 13 is a close up cross-sectional view of an area of an illustrative implementation of a rotary blood pump with an axial hydrodynamic bearing.

FIG. 13 is a close up cross-sectional view of an area D of an illustrative implementation of pump 120. Each arc shaped segment 127 of impeller 125 includes one or more pattern grooves on top surfaces 165. The pattern grooves on top surface 165 of impeller 125 and internal surface 155 of housing 150 form a hydrodynamic bearing providing partial axial hydrodynamic support that prevents or minimizes contact between impeller 125 and housing 150. The pattern grooves on top surface 165 are considered to be interrupted because they are separated by the flow channels of impeller 125.

Figure 12A:
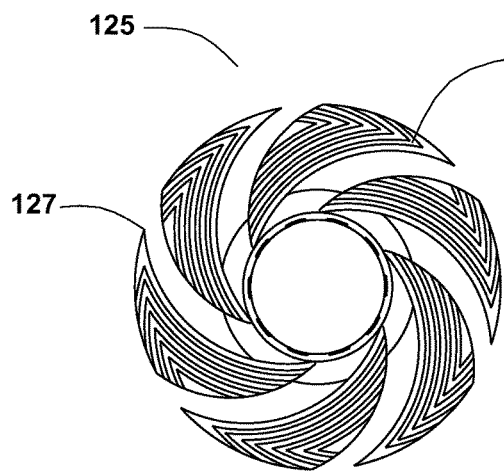
FIGS. 12A and 12B are top views of illustrative implementations of impellers with spiral herringbone grooves and spiral grooves.
Figure 12B:
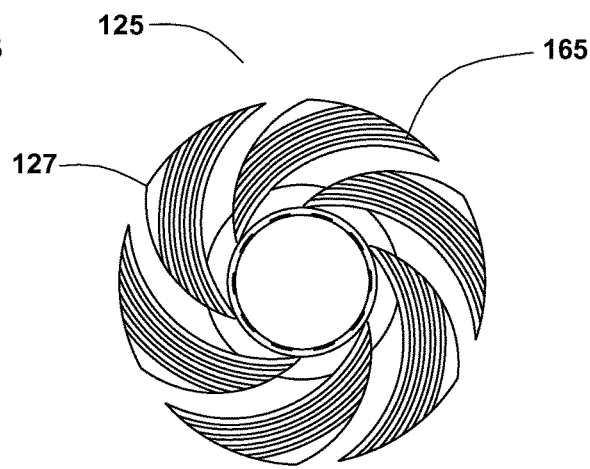
Figure 14A:
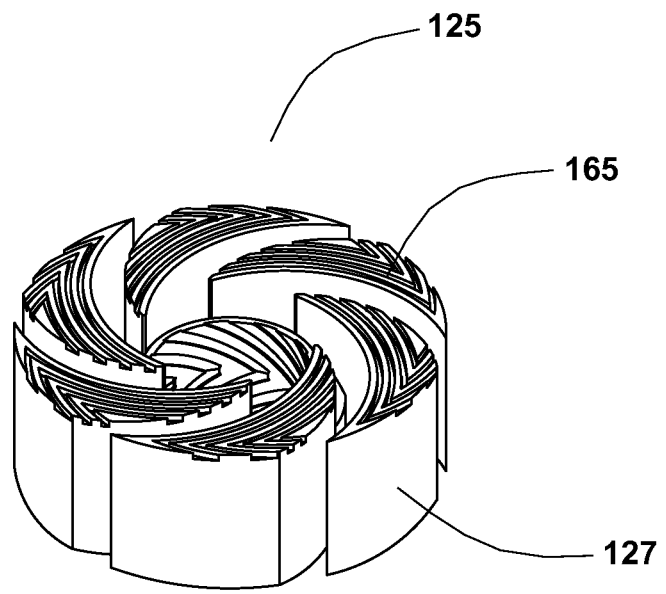
FIGS. 14A and 14B are isometric views of illustrative implementation of impellers with spiral herringbone grooves and spiral grooves.
Figure 14B:
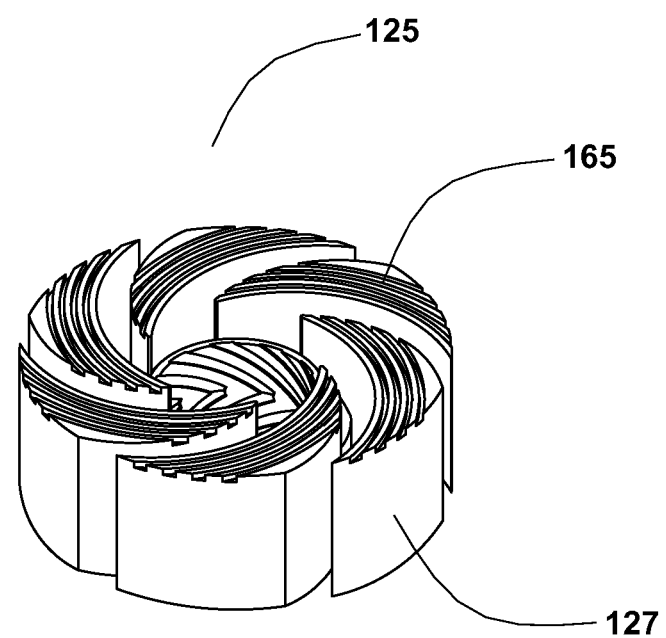
Figure 16A:
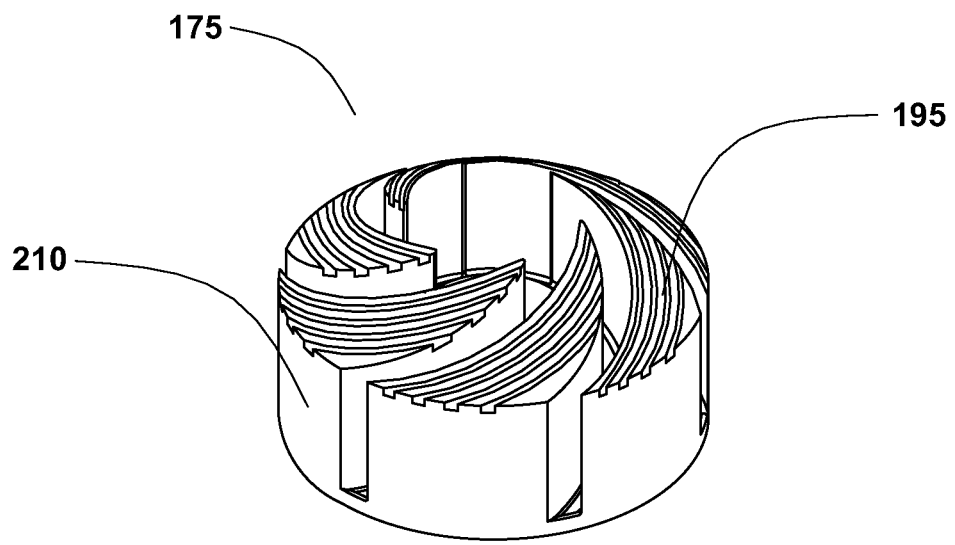
FIG. 16A-16E are isometric views of illustrative implementations of conically shaped impellers.

Pattern grooves on top surface of impeller 125 may be any suitable type of grooves including, but not limited to, spiral herringbone and spiral grooves shown in FIGS. 12A and 12B. FIGS. 14A and 14B respectively provide an isometric view of impeller 125 with spiral herringbone and spiral grooves. The arrangement of the pattern grooves on top surfaces 165 is balanced so that instability during rotation of impeller 125 is prevented or minimized. For example, all of the top surfaces 165 have pattern grooves in the implementation shown. However, it should be recognized that in other implementations a balanced arrangement of top surfaces 165 that have pattern grooves and do not have pattern grooves may be utilized. A balanced arrangement of top surfaces 165 prevents or minimizes the instability of impeller 125. Examples of balanced arrangements for the implementation shown may include, but are not limited to, all top surfaces 165 with grooves or three alternating top surfaces 165 with grooves and three without grooves. Flow inducing pattern grooves, such as spiral and spiral herringbone grooves, have the added benefit of producing a substantial secondary flow, particularly between top surface 165 of impeller 75 and internal surface 155 of housing 150. Additionally, various pattern groove types including symmetrical, asymmetrical, open, and/or dual groove patterns and various groove shapes including rectangular, rectangular with a bevel, semi-circular, and elliptical shown in FIGS. 9A-9K and 10A-10D may be utilized. An additional benefit of the hydrodynamic bearing on top surface 165 of impeller 125 is that it increases impeller stability during rotation by restraining angular motion along axes normal to the axis of impeller rotation.

Figure 15:
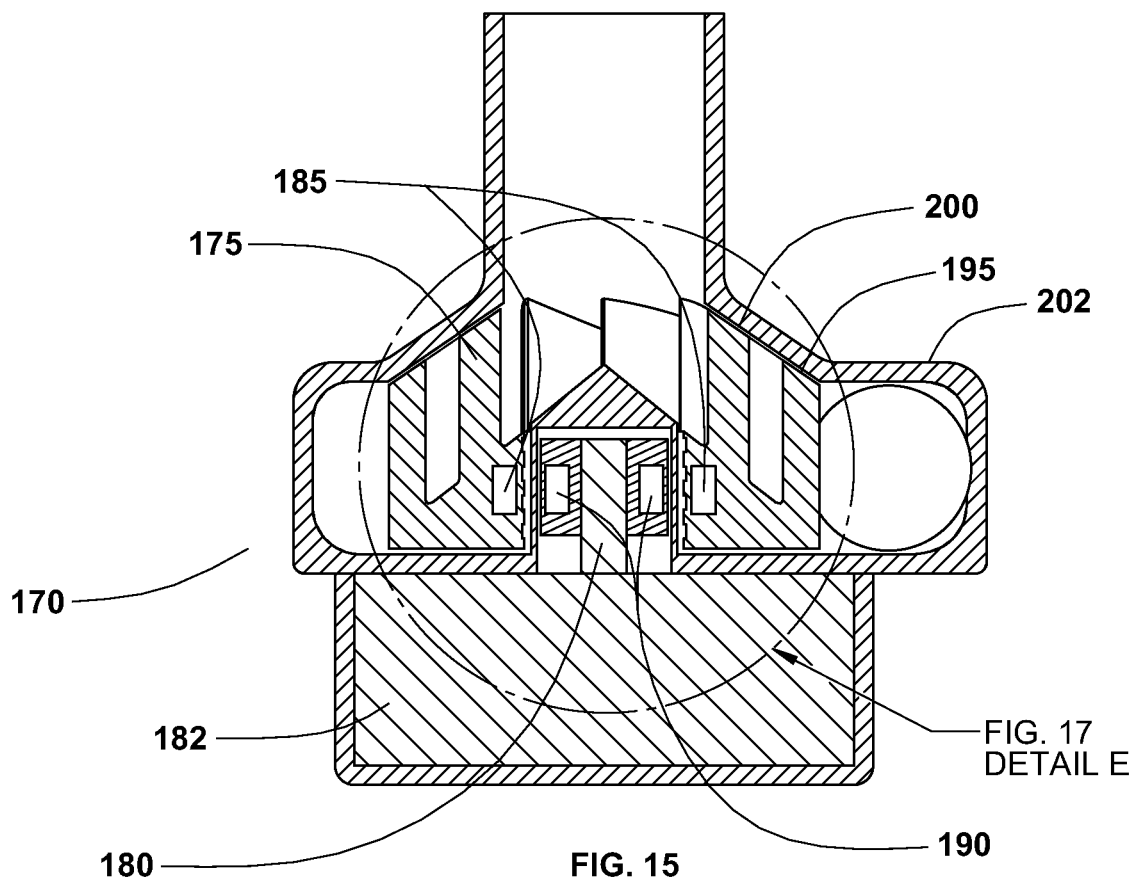
FIG. 15 is a cross-sectional side view of an illustrative implementation of a rotary blood pump with a conically shaped impeller.

FIG. 15 is a cross-sectional side view of an illustrative implementation of pump 170 with a conically shaped impeller 175. Many of the components of pump 170 are substantially similar to the components of the previously discussed illustrative implementations. These similar components may operate in substantially the same manner as previously described. As in the previously discussed implementations, impeller 175 is magnetically coupled to shaft 180 of motor 182. Permanent magnets 185 and 190 couple motor 182 to impeller 175. However, in the implementation shown, impeller 175 is formed in a generally conical shape. Top surfaces 195 of impeller 175 facing internal surface 200 of the pump housing 202 are shaped in a manner that provides a hydrodynamic bearing between impeller top surfaces 195 and internal surface 200.

Figure 16B:
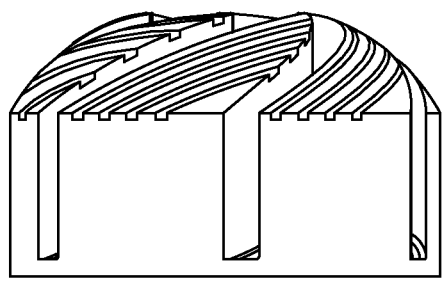
Figure 16C:
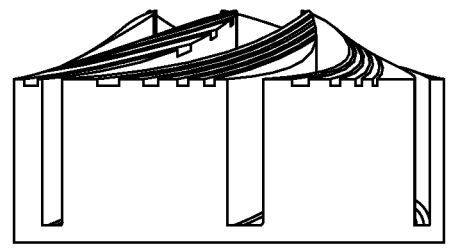
Figure 16D:
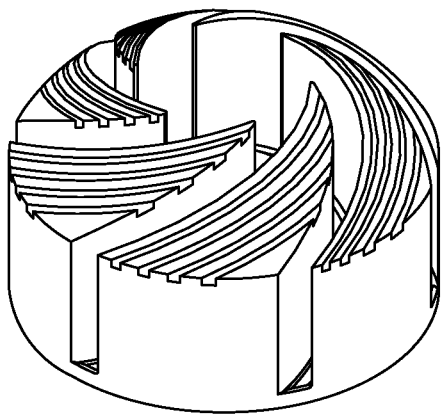
Figure 16E:
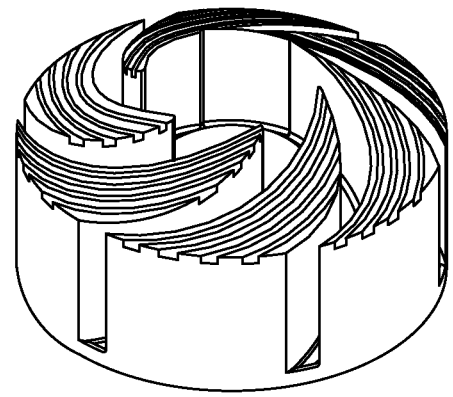
Figure 17:
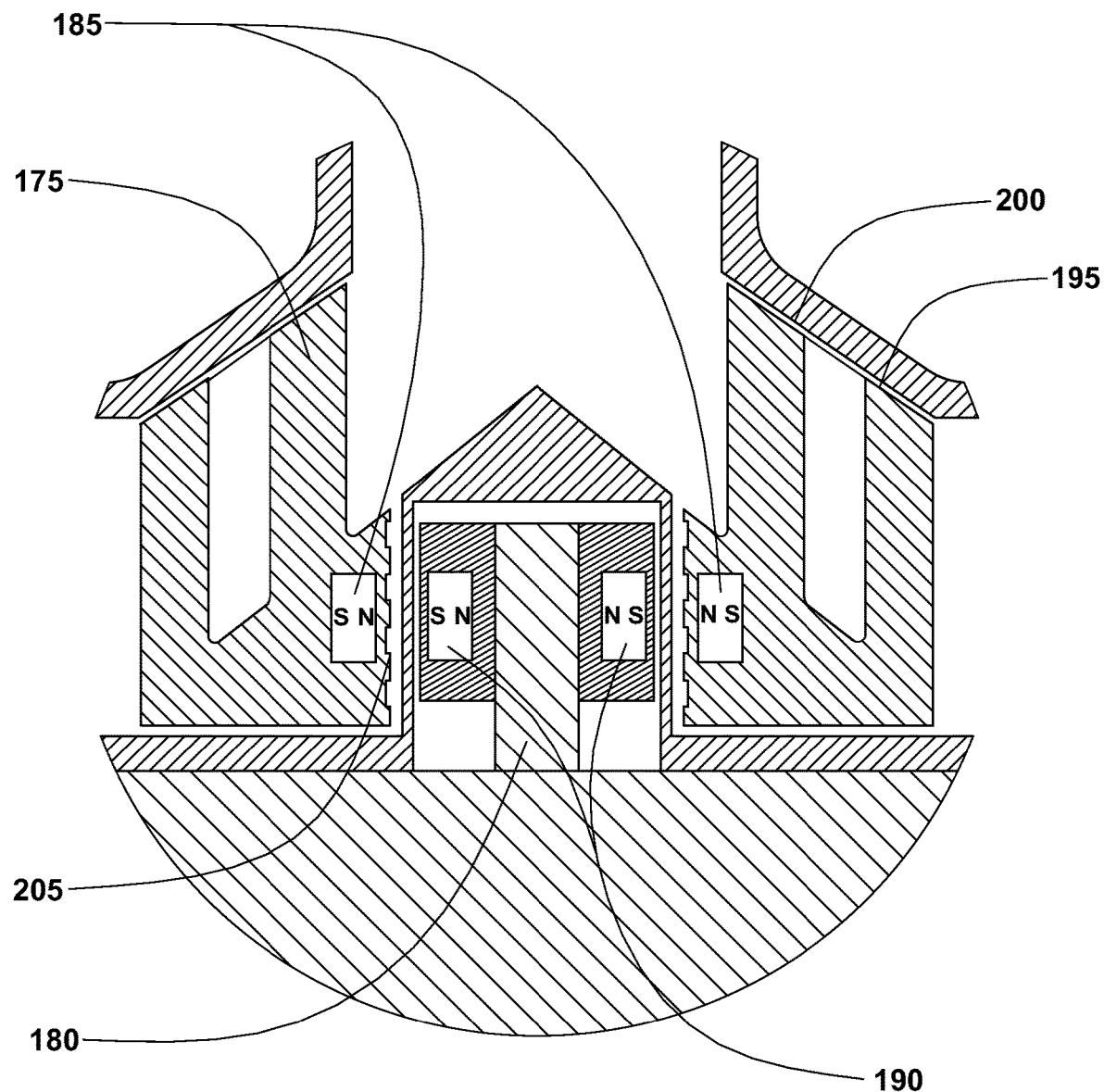
FIG. 17 is a close up cross-sectional view of an area of an implementation of a rotary blood pump with a conically shaped impeller.

FIG. 17 is a close up cross-sectional view of an area E of an illustrative implementation of pump 170. As in the other implementations previously discussed, internal surface 205 of impeller 175 may include pattern grooves for a hydrodynamic bearing providing radial support. Top surfaces 195 of impeller 175 are angled to provide a generally conical shaped impeller 175. FIGS. 16A-16E are views of various implementations of impeller 175. Impeller 175 has multiple blade segments 210 that each have a top surface 195. Top surfaces 195 of blade segments 210 may be linear (FIG. 16A), convex (FIG. 16B), or concave (FIG. 16C) surfaces. Additionally, FIGS. 16D-16E are views of impeller 175 with convex and concave top surfaces 195.

One or more of the top surfaces 195 of impeller 175 may incorporate interrupted pattern grooves of any type including, but not limited to, spiral or spiral herringbone grooves. For example, the interrupted pattern grooves may be similar to the pattern grooves shown in FIGS. 12A and 12B. The arrangement of the pattern grooves on top surfaces 195 is balanced so that instability during rotation of impeller 175 is prevented or minimized. For example, all of the top surfaces 195 have pattern grooves in the implementation shown. However, it should be recognized that in other implementations a balanced arrangement of top surfaces 195 that have pattern grooves and do not have pattern grooves may be utilized. Flow inducing pattern grooves, such as spiral and spiral herringbone grooves, have the added benefit of producing a substantial secondary flow, particularly between top surface 195 of impeller 175 and internal surface 200 of pump housing 202. Additionally, various pattern groove types including symmetrical, asymmetrical, open, and/or dual groove patterns and various groove shapes including rectangular, rectangular with a bevel, semi-circular, and elliptical may alternatively be utilized as shown in FIGS. 9A-9K and 10A-10D. In some implementations, top surfaces 195 of impeller 175 do not utilize pattern grooves. For example, the conical shaped impeller 175 may be a pressure balanced type impeller where the magnetic coupling formed by magnets 185 and 190 provides sole axial restraint of impeller 175.

In addition to the axial restraint provided by the magnetic coupling discussed previously, the hydrodynamic bearing provided by top surfaces 195 of impeller 175 partially restrains axial movement in the direction along the axis of rotation. Because top surfaces 195 are angled, the hydrodynamic bearing of top surfaces 195 also partially restrains radial motion of impeller 175. Thus, the hydrodynamic bearing of top surfaces 195 provides partial radial and axial support for impeller 175. The hydrodynamic bearings of top surface 195 and impeller internal surface 205 and the partial restraint provided by the magnetic coupling increase impeller stability during rotation by restraining axial and radial motion.

Figure 18:
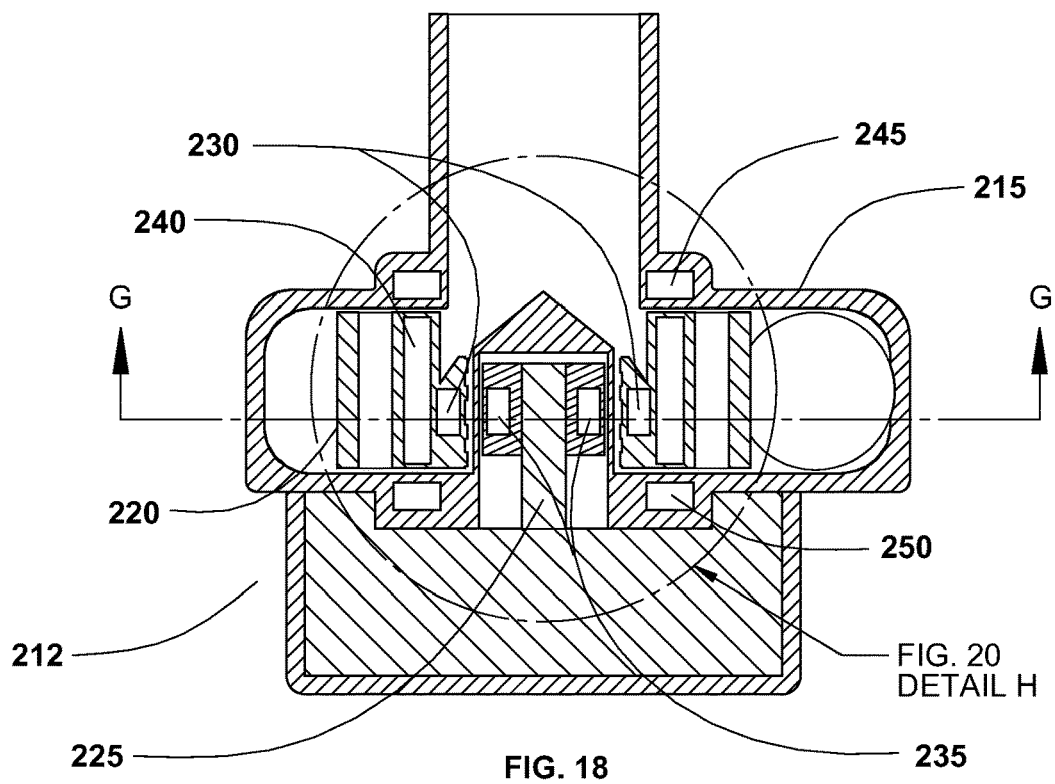
FIG. 18 is a cross-sectional side view of an illustrative implementation of a rotary blood pump with passive magnetic axial bearings.

FIG. 18 is a cross-sectional side view of an illustrative implementation of pump housing 215 for pump 212. Many of the components of pump 212 are substantially similar to the components of the previously discussed illustrative implementations. These similar components may operate in substantially the same manner as previously described. As in the previously discussed implementations, impeller 220 is magnetically coupled to shaft 225. Permanent magnets 230 and 235 couple the motor to impeller 220.

Figure 20:
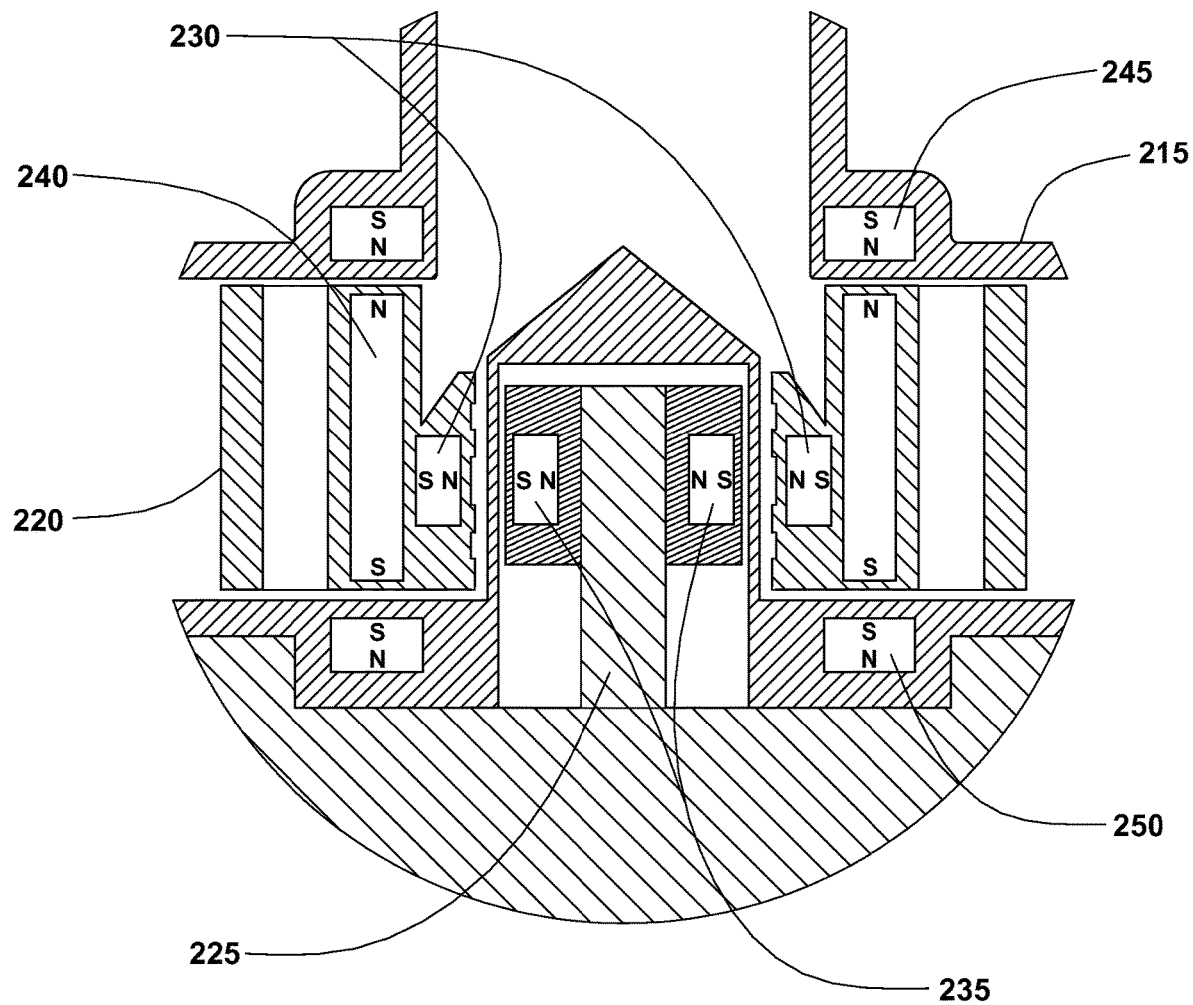
FIG. 20 is a close up cross-sectional view of an area of an illustrative implementation of a rotary blood pump with passive magnetic axial bearings.

Impeller 220 contains permanent magnets 240 and pump housing 215 contains permanent magnets 245, 250 thereby forming a magnetic thrust bearing for minimizing axial movement of impeller 220. Permanent magnets 245, 250 in housing 215 may be one or more magnets formed into a ring. FIG. 20 is a close up cross-sectional view of an area H of an illustrative implementation of pump 212. Permanent magnets 240 in impeller 220 and permanent magnets 245 in the top portion of pump housing 215 are arranged to provide a repulsive force between impeller 220 and pump housing 215. Permanent magnets 240 in impeller 220 and permanent magnets 250 in the bottom portion of pump housing 215 are also arranged to provide a repulsive force between impeller 220 and pump housing 215. The axial restraint forces generated by magnets 240, 245, 250 are significantly greater than the attractive forces generated by the permanent magnets 230 and 235 and thereby provide sole axial support with greater stiffness for impeller 220 during rotation. Magnets 240 in impeller 220 and magnets 245, 250 in pump housing 215 provide large axial restraint forces to allow for increased clearances between impeller 220 and pump housing 215 during rotation. The increased clearances reduce damage to blood and allow for increased flow through the clearances during impeller rotation.

Figure 19:
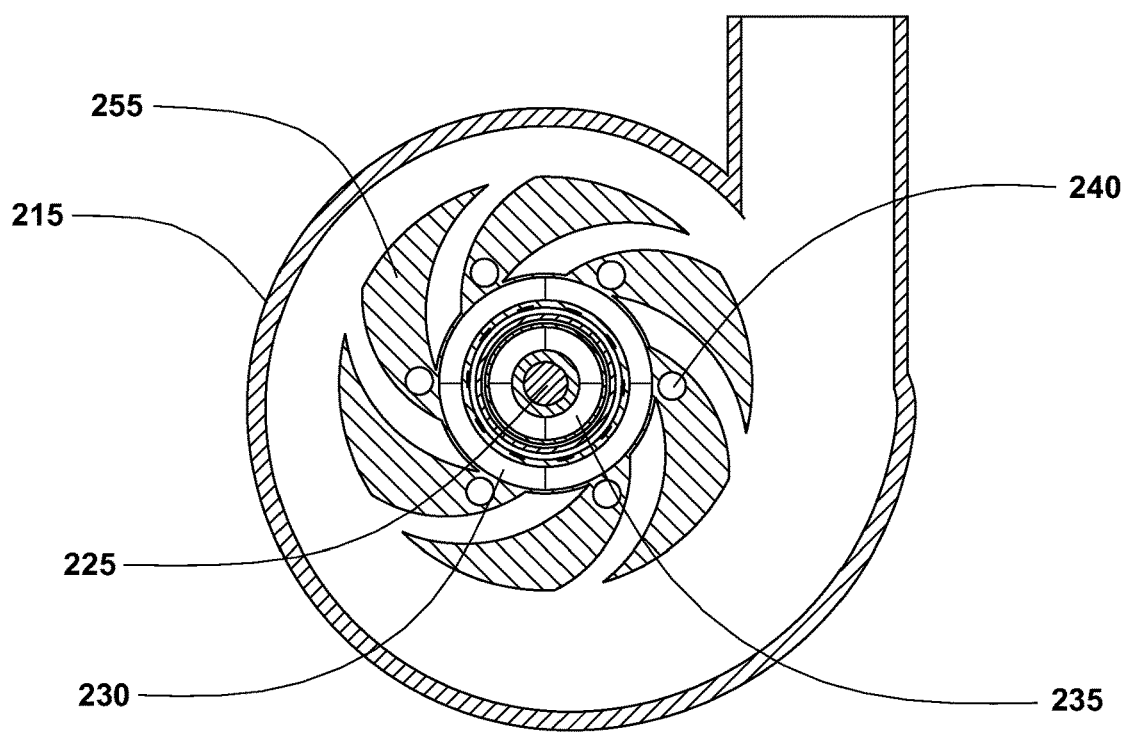
FIG. 19 is a cross-sectional top view of an illustrative implementation of a rotary blood pump with passive magnetic axial bearings.

FIG. 19 is a cross sectional top view of an illustrative implementation of pump 212. Magnets 240 are arranged radially around impeller 220. Each blade segment 255 of impeller 220 may provide an opening/region for receiving one or more magnets 240. Additionally, in some implementations, the top and/or bottom surfaces of impeller 220 may incorporate various pattern groove types including spiral, spiral herringbone, symmetrical, asymmetrical, open, and/or dual groove patterns. Further, various groove shapes including rectangular, rectangular with a bevel, semi-circular, and elliptical may also be utilized as shown in FIGS. 9A-9K and 10A-10D.

Implantable Power Module and Wireless Power Transfer Subsystem

An implantable power module may provide energy storage to power an implantable rotary blood pump. Some currently available power modules are worn externally and may require a percutaneous wire penetrating the patient's skin to power the implanted rotary blood pump. Other available cardiac support systems that do not require a percutaneous wire may utilize inductive energy transfer to power the implanted blood pump wirelessly. These systems may also utilize implanted batteries to power the blood pump when inductive energy transfer is not provided. However, due to the high power consumption of the implanted blood pump and/or other components, these systems are only capable of operation for a short duration using power from implanted batteries that have been fully charged. For example, the LionHeart LVD-2000 utilizes short range inductive charging and is capable of approximately 20 minutes of operation using power provided by an implanted battery. In contrast, the implantable power module described herein is capable of operating the implanted rotary blood pump for an entire day of awake hours using power provided by the energy storage device contained within the power module implanted in the patient. The wireless power transfer subsystem described herein is capable of providing power, without the need for percutaneous wires, to operate the implanted blood pump and simultaneously recharge the implanted energy storage device during a normal sleep period of 8 hours or less. Moreover, the wireless power transfer subsystem is capable of providing power using short range inductive energy transfer or mid range energy transfer using magnetic resonance coupling (MRC).

Figure 21:
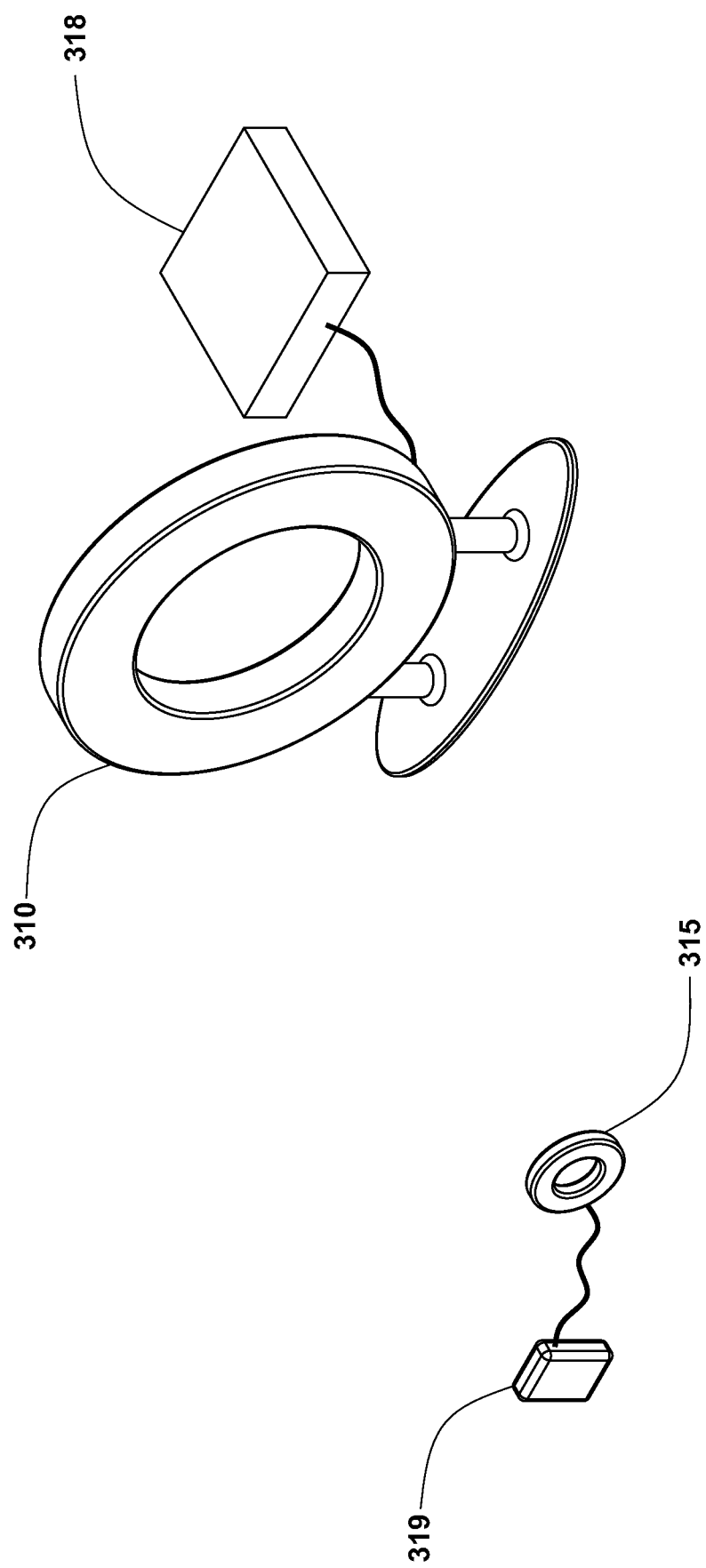
FIG. 21 is an illustrative implementation of a wireless power system.
Figure 22:
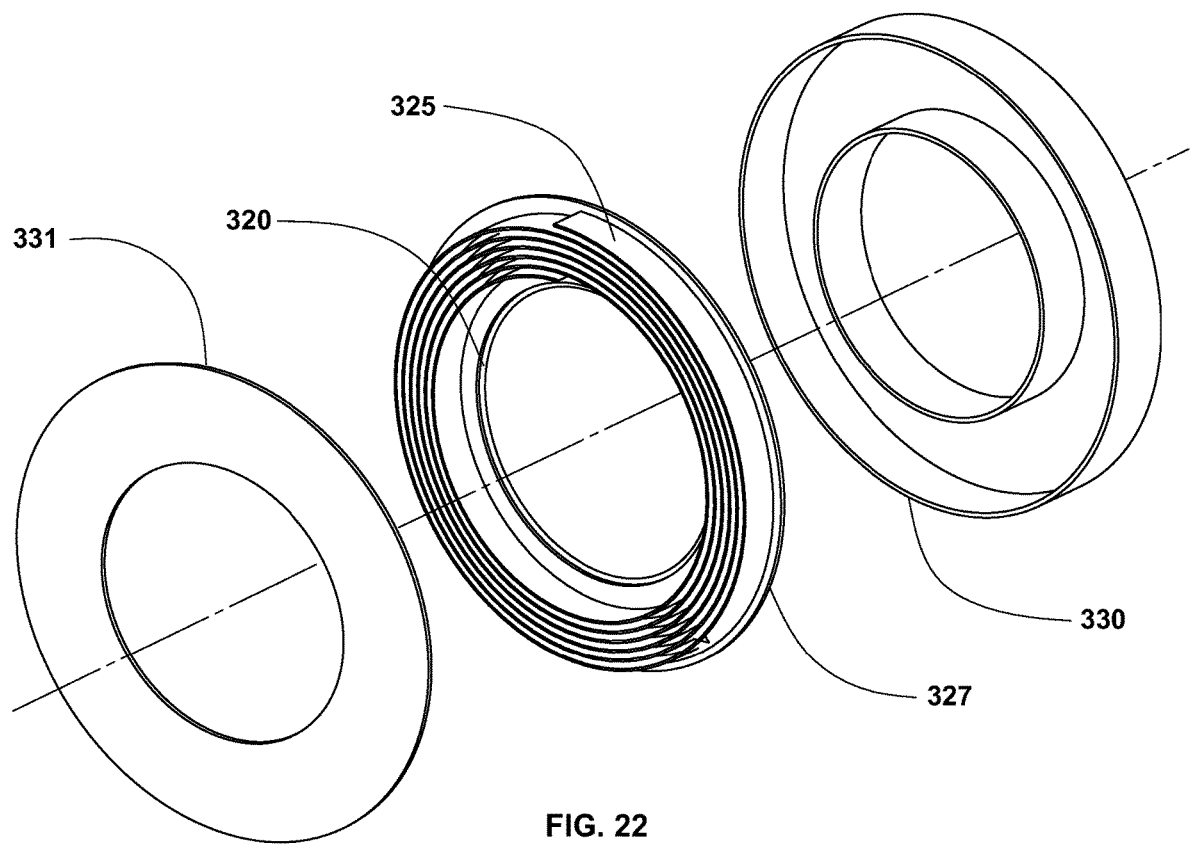
FIG. 22 is an isometric view of an illustrative implementation of a transmitting coil assembly.
Figure 23:
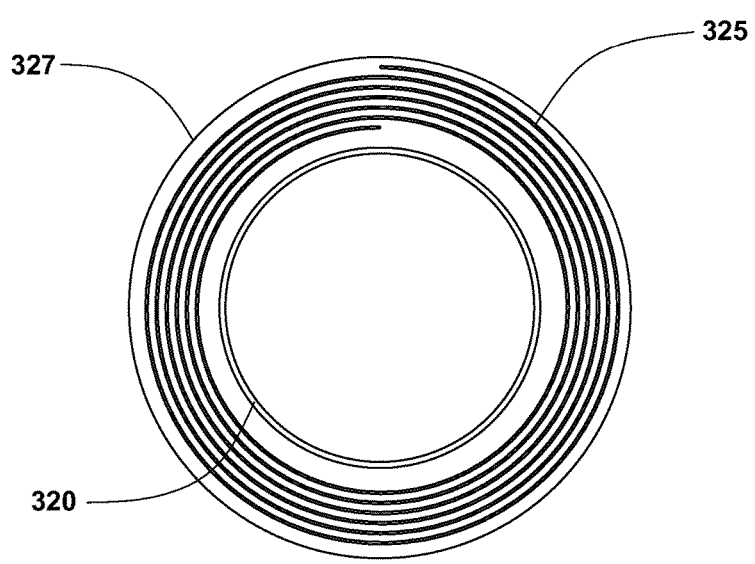
FIG. 23 is a front view of an illustrative implementation of a transmitting resonant coil and excitation coil.
Figure 24:
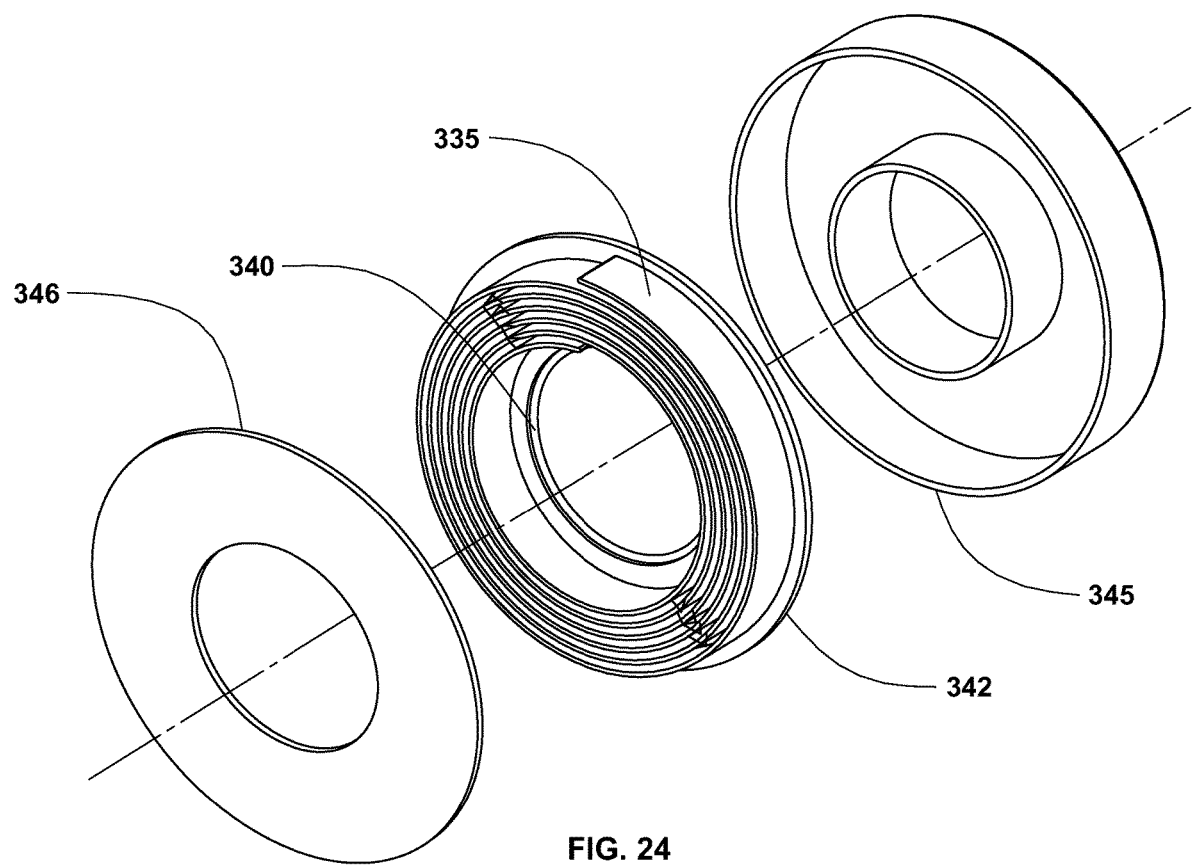
FIG. 24 is an isometric view of an illustrative implementation of a receiving coil assembly.

FIG. 21 is an isometric view of an illustrative implementation of a wireless power subsystem and power module for a cardiac support system. Wireless power subsystem and power module may include transmitting coil assembly 310, receiving coil assembly 315, RF power supply 318, and power module 319. In some implementations, receiving coil assembly 315 and power module 319 may be implanted in a patient. Receiving coil assembly 315 and power module 319 may be provided in the same or separate hermetically sealed biocompatible housing(s). FIG. 22 is an isometric view of an illustrative implementation of a transmitting coil assembly 310. Transmitting coil assembly 310 may include an excitation coil 320, transmitting resonant coil 325, mounting plate 327, housing 330, and cover 331. FIG. 23 is a front view of an illustrative implementation of transmitting resonant coil 325, excitation coil 320, and mounting plate 327. Excitation coil 320 is placed close enough to transmitting resonant coil 325 to be inductively coupled such that when high frequency AC power, such as that from an RF power supply 318 shown in FIG. 21, on the order of 30 KHz-15 MHz is supplied to excitation coil 320, this causes transmitting resonant coil 325 to resonate resulting in a local time varying magnetic field. This resonant magnetic field interacts with a resonant coil provided by receiving coil assembly 315 as shown in FIG. 24. This resonant magnetic field interaction between the transmitting resonant coil 325 and a resonant coil provided by receiving coil assembly 315 is referred to as magnetic resonance coupling.

Magnetic resonance coupling is a phenomenon in which two resonant objects tuned to the same or similar frequency electromagnetically exchange energy strongly but interact only weakly with other non-resonant objects. For example, magnetic resonance coupling may allow energy to be transferred wirelessly between two resonant coils over significant distances, whereas inductive coupling requires the two coils to be placed close to each other.

Figure 25:
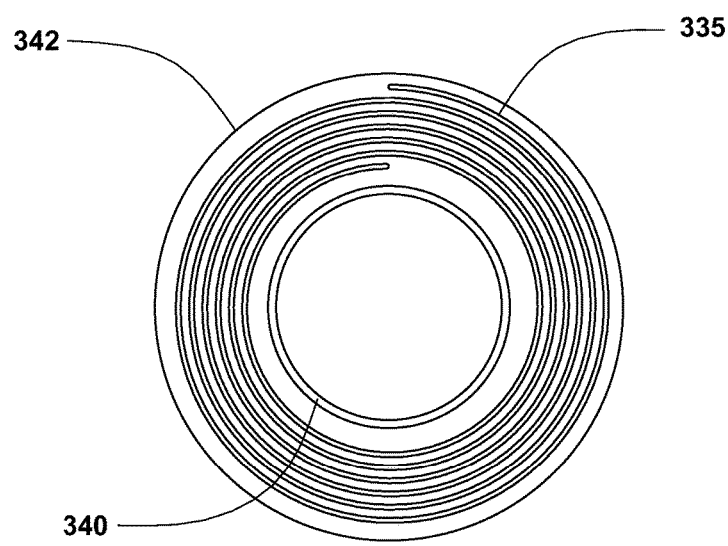
FIG. 25 is a front view of an illustrative implementation of a receiving resonant coil and power pick-up coil.

FIG. 24 is an isometric view of an illustrative implementation of a receiving coil assembly 315. Receiving coil assembly 315 provides a receiving resonant coil 335, power pick-up coil 340, mounting plate 342, hermetically-sealed biocompatible housing 345, and cover 346. FIG. 25 is a front view of an illustrative implementation of receiving resonant coil 335, power pick-up coil 340, and mounting plate 342. Excitation coil 320 and power pick-up coil 340 may be made from a minimal number of conductor loops, and with any suitable conductor material, such as stranded or solid copper wire, so as not to produce too strong inductive coupling to their respective resonant coils 325 and 335 and thereby minimize the effect on resonant coil natural frequency and Q factor as discussed further below. Housing 345 and cover 346 are made of a biocompatible material. Housing 345 and cover 346 secure and seal receiving coil assembly 315. Note that in other implementations, receiving resonant coil 335 may be separated from receiving coil assembly 315 as discussed in further detail below.

Transmitting resonant coil 325 and receiving resonant coil 335 are designed to have closely matched or identical natural resonant frequencies as defined by equation 1.

$$\omega = \sqrt{\frac{1}{LC}} \quad [1]$$

where, ω=coil natural resonant frequency (radians)
L=coil inductance (Henries)
C=coil capacitance (Farads)

By doing so, the magnetic field produced by transmitting resonant coil 325 causes receiving resonant coil 335 to strongly resonate also, generating its own local time varying magnetic field, and thereby achieves magnetic resonance coupling between the transmitting and receiving coils. In such a system, power may be transferred wirelessly and efficiently through this magnetic resonance coupling over a much greater distance than that of currently known traditional inductive coupling. Power pick-up coil 340 is placed close enough to receiving resonant coil 335 so as to receive energy from receiving resonant coil 335 inductively, causing an AC voltage across power pick-up coil 340. This AC voltage can then be rectified to a DC voltage and used to power an implantable medical device and/or recharge implantable batteries.

The amount of energy that can be transferred to receiving resonant coil 335 is proportional to the strength of magnetic field emitted from transmitting resonant coil 325. The strength of the magnetic field emitted from transmitting resonant coil 325 should be maximized for a given amount of energy input to excitation coil 320 to optimize system efficiency and power transfer as well as minimize receiving coil assembly 315 size. This is accomplished by choosing a drive frequency F that is closely matched or identical to the natural resonant frequencies ω of transmitting 325 and receiving 335 resonant coils and by increasing resonant coil quality factor Q, given by equation 2:

$$Q = \sqrt{\frac{L}{C}} * \frac{1}{R} \quad [2]$$

where, Q=coil quality factor
L=coil inductance (Henries)
C=coil capacitance (Farads)
R=coil AC resistance (Ohms) at resonant frequency ω (radians)

Each resonant coil should have a Q factor sufficiently high in order to provide reasonably efficient energy transfer. The diameter and placement of excitation coil 320 in relation to transmitting resonant coil 325 can be a variety of different sizes and arrangements, as the transmitting coil assembly does not have the same size and space constraints as the receiving coil assembly. In some implementations, it may be desirable to make the diameter of excitation coil 320 smaller than transmitting resonant coil 325, such that the natural resonant frequency and Q factor of transmitting resonant coil 325 is minimally affected by excitation coil 320 when placed within the enclosed volume of transmitting resonant coil 325, as shown in FIG. 22. However, in other implementations, the diameter of excitation coil 320 may be larger than transmitting resonant coil 325 and/or excitation coil 320 may be angled or out of plane with transmitting resonant coil 325 to minimize effects on the natural resonant frequency and Q factor of transmitting resonant coil 325.

One or more components of the receiving coil assembly may be implanted into the human body. Thus, it may be desirable to minimize the size of receiving resonant coil 335 and/or power pick-up coil 340 to be implanted. For example, the size of a receiving coil assembly may be minimized by placing power pick-up coil 340 within the enclosed volume of receiving resonant coil 335. The outer diameter of power pick-up coil 340 can be made smaller than the outer diameter of receiving resonant coil 335, such that the natural resonant frequency and Q factor of receiving resonant coil 335 is minimally affected by power pick-up coil 340 when placed within the enclosed volume of receiving resonant coil 335. This provides an optimum state of system tuning for maximum power transfer and efficiency while minimizing receiving coil assembly thickness and/or volume. It is important to achieve a receiving coil assembly 315 that is thin and implantable to allow for easy implantation and less noticeable implant site for patient comfort and well being. For example, in well tuned systems, receiving coil assembly 315 may be one inch or less in overall thickness. Note that in some implementations, receiving resonant coil 335 and power pick-up coil 340 may be separated so that the receiving coil assembly implanted in the patient comprises power pick-up coil 340 and not receiving resonant coil 335. Such an arrangement would minimize the size of components that are implanted in the patient, but would require receiving resonant coil 335 to be placed near the location where power pick-up coil 340 is implanted.

As can be seen in equations 1 and 2, the factors affecting the coil quality factor Q are coil inductance, capacitance, AC resistance, and resonant frequency. Specifically, to maximize Q factor, the coil inductance and resonant frequency should be maximized while the coil capacitance and AC resistance should be minimized. However, as can be seen in equation 1, coil inductance and capacitance must be chosen correctly to achieve a desired coil natural resonant frequency. For the implantable wireless power transfer subsystem disclosed herein, the desired coil natural resonant frequency is between 30 KHz-15 MHz.

One method that can be utilized to increase coil inductance is to provide more coil turns at larger coil diameters. However, more coil turns and larger coil diameters require longer conductor lengths thereby increasing coil AC resistance and decreasing the benefit of higher inductance on coil Q factor. Furthermore, conductor lengths greater than $\frac{1}{10}^{th}$ of the resonant frequency wavelength λ may adversely impact performance due to wave reflections. Additionally, more coil turns further increase coil AC resistance because of proximity effect. Proximity effect is a well known phenomenon in which the local magnetic fields of adjacent coil turns cause current flow to be constrained to smaller and smaller conductor areas as more coil turns are added. The net effect is that a decreasing portion of available conductor area is utilized as more coil turns are added. For example, the AC resistance of a coil with 4 turns can be several times higher than a coil of the same average diameter with only 2 turns, even if the conductor length of the 4 turn coil is only twice that of the 2 turn coil.

Another phenomenon that increases coil AC resistance relative to DC resistance is the skin effect. Skin effect is caused by the internal magnetic fields generated within a single turn of conductor, as opposed to proximity effect caused by multiple conductor turns. Skin effect is similar to proximity effect in that a decreasing portion of available conductor area is utilized as AC operating frequency is increased. This results in current flow that is more concentrated at the outer surfaces of a conductor as opposed to the interior portion of a conductor. The depth to which most of the current flow is constrained in a conductor operating at a given AC frequency is known as the skin depth and is given by equation 3:

$$\delta = \sqrt{\frac{2\rho}{f\mu}} \quad [3]$$

where, δ=skin depth (meters)
ρ=resistivity of conductor (Ohm-meters)
f=operating frequency (radians)
μ=absolute magnetic permeability of conductor (Henries/meter)

Therefore, it can be seen for a conductor of thickness T that is much thicker than the skin depth δ, most of the conductor is not utilized to pass AC current. The ratio of conductor thickness T to skin depth δ is known as the skin depth ratio. It is clear that increasing conductor thickness T above skin depth δ does little to reduce the AC resistance of a conductor, but merely increases coil volume and mass. However, it also does not make the skin effect worse.

Notably, it is known in close coupled AC inductive transformer design that increasing conductor thickness T far above skin depth δ can worsen the proximity effect substantially, especially as more coil turns are added. For example, a high skin depth ratio above 2 can cause the AC resistance of an inductive transformer coil to be greater than 10 times higher than the same coil with a skin depth ratio of 1 or less, depending on the number of coil turns employed and operating frequency. Therefore, the conductor thickness T used in transmitting 325 and receiving 335 resonant coils is chosen to produce a skin depth ratio of less than or equal to 2 to minimize proximity effects, reduce coil AC resistance, and increase coil quality factor Q. Similarly, a skin depth ratio less than one may be advantageous. In one implementation, copper or silver foil of a thickness less than 0.020 inches is used. Counter intuitively, thin copper foil produces less AC resistance than thick copper foil for some of the operating frequencies disclosed herein. By utilizing a thin conductor, it is believed that a quality factor of 100 or greater may be achieved. In experiments using thin copper foil, a receiving resonant coil 335 with a quality factor above 300 for a coil size 3 inches or less in diameter and 0.5 inches or less in width has been achieved, which would result in a receiving coil assembly sufficiently small to implant. A receiving resonant coil 335 of the size above would then allow the entire receiving coil assembly to be less than 1 inch thick. Such a receiving resonant coil 335 may enclose an area of 7.1 in$^2$ or less. Further, the total volume of receiving resonant coil 335 may be 7.1 in$^3$ or less. Additionally, this may result in a transmitting resonant coil 325 with a quality factor above 600 for a coil size 6 inches or greater in diameter and one inch or less in width. Such a transmitting resonant coil 325 may enclose an area of 28.3 in$^2$ or more. Further, the total volume of transmitting resonant coil 325 may be 28.3 in$^3$ or more. Using the foregoing transmitting 325 and receiving 335 resonant coil diameters may result in a transmitting/receiving resonant coil diameter ratio of 2:1 or greater which may allow adequate power to be transferred over a distance equal to or greater than the diameter of receiving resonant coil 335. In experiments, we have achieved adequate power transfer over distances greater than five times the diameter of the receiving coil. Such a system design is uniquely suited for implantable wireless power systems and methods. Unlike traditional inductive coupling, such systems and methods may be capable of transmitting adequate power even when transmitting and receiving coils are laterally or angularly misaligned to a large extent, such as when a patient is sleeping.

As shown in equation 1, once the inductance of resonant coil 325 or 335 is fixed, the proper capacitance must be present for the coil to resonate at a desired frequency co. Coil capacitance can either be intrinsic, added in the form of a fixed or variable capacitor, or both intrinsic and added. Intrinsic capacitance is that which is formed by the coil geometry itself. For example, a coil with turns made from copper or silver foil separated by one or more insulating dielectric materials such as PTFE, low-loss PTFE, polyethylene, polypropylene, vacuum, an inert gas, or air could be analogous to a flat plate capacitor of equal plate area and plate separation distance. However, intrinsic coil capacitance cannot be calculated in the same manner as a flat plate capacitor due to the effect of multiple turns. Many dielectric materials, such as those listed previously, are suitable to provide this intrinsic capacitance; however it is important that the materials have a low dielectric dissipation factor to not detrimentally impact the overall coil Q factor. To maintain an overall coil Q factor sufficiently high for adequate power transfer, the one or more insulating materials should have a dielectric dissipation factor of 0.01 or less at the coil resonant frequency.

It is desirable for transmitting 325 and receiving 335 resonant coils to have as little intrinsic capacitance as possible, if the intrinsic capacitance is formed partially or fully by a solid dielectric material. This is done to minimize the temperature sensitivity of the resonant coils which can shift their resonant frequencies and detune the system, resulting in lost power and efficiency. One method that can be utilized to assist in stabilizing the resonant frequency of receiving resonant coil 335 is to maintain receiving resonant coil 335 at a relatively constant temperature, such as that provided by implanting inside the human body at a temperature of 37+/−5 degrees C. Additionally, transmitting resonant coil 325 may be maintained at a relatively constant temperature of 25+/−5 degrees C. with the use of cooling fans contained in durable housing 330.

Figure 26B:
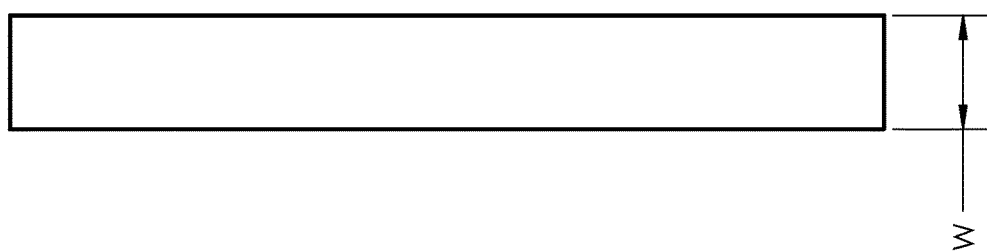
FIGS. 26a and 26b are front and side views of illustrative implementations of a resonant coil with single wrap conductive foil.
Figure 26A:
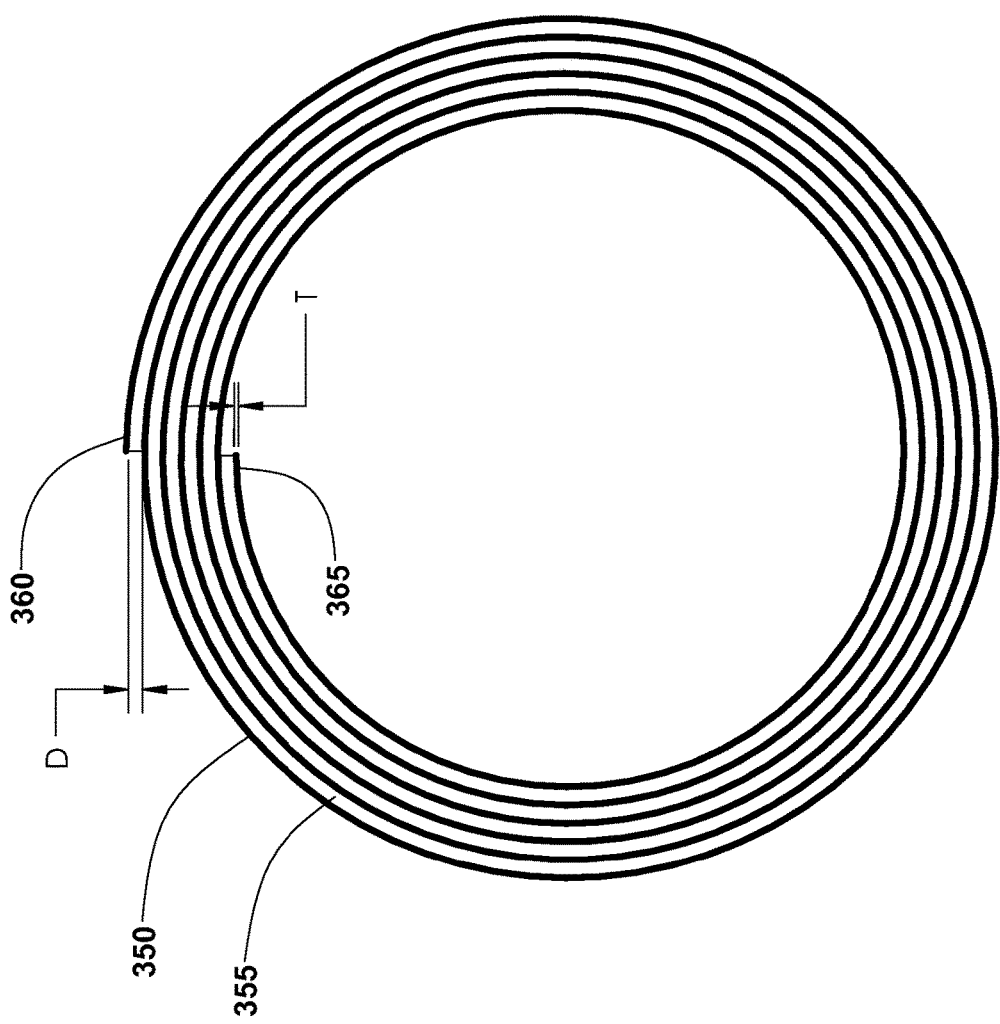

FIGS. 26a and 26b are front and side views of illustrative implementations of a resonant coil, such as transmitting or receiving resonant coil, with single wrap conductive foil. In one implementation, resonant coils 325 and 335 achieve very low intrinsic capacitance using a flat conductor geometry, such as conductive foil 350 constructed from one or more high conductivity materials such as copper or silver, separated by an insulating medium 355 composed of one or more low dielectric constant materials such as PTFE, low-loss PTFE, polyethylene, polypropylene, vacuum, an inert gas, air, or any combination thereof with relatively large spacing D between turns as shown in FIG. 26a. As described previously, the one or more insulating materials should have a dielectric dissipation factor of 0.01 or less at the coil resonant frequency to maintain an overall coil Q factor sufficiently high for adequate power transfer. Spacing D indicates the total thickness of the insulating medium 355. In some implementations, insulating medium 355 may be composed of at least one solid material with a polygonal cross section that also provides mechanical support for the conductive foil 350. A polygonal cross section, defined as a cross sectional shape with all straight sides, is chosen as it is a readily available form of PTFE, low loss PTFE, polyethylene, and polypropylene and results in a volume efficient resonant coil assembly. In the side view shown in FIG. 26b, width W may indicate the width of the conductive foil 350 and insulating medium 355. The amount of capacitance can be varied by increasing/decreasing the spacing D between coil turns or increasing/decreasing the conductor width W. Spacing D can be kept constant or varied between any adjacent turns so long as it results in the desired low intrinsic capacitance. One or more fixed or variable external capacitors with low temperature sensitivity may be added across the start and end of the coil turns to tune the coil to a desired resonant frequency. Low dielectric dissipation factor external capacitors should be used so that when combined with the insulating medium 355, the combined dielectric dissipation factor of the external capacitors and insulating medium 355 is low to maintain an overall coil Q factor sufficiently high for adequate power transfer. Low temperature sensitivity external capacitance with a temperature coefficient of less than 3000 ppm/degree C. should be used and the external capacitance should be at least one tenth the intrinsic capacitance to positively impact the thermal stability of the overall coil capacitance. The start 360 and end 365 of conductive foil 350 may be approximately within 45 degrees of each other to minimize external capacitor lead length.

In an illustrative implementation, conductive foil 350 used in resonant coils 325 and 335 is chosen with a thickness T, such that the skin depth ratio is less than 2 for a given operating resonant frequency between 30 kHz-15 MHz. This is done to decrease the coil AC resistance and thereby increase coil Q factor. To further decrease coil resistance, the conductive foil 350 may be provided on both sides of an electrically non-conductive round or rectangular spiral coil form, made from material such as ABS or polycarbonate. For example, the electrically non-conductive round or rectangular spiral coil form may be double wrapped by adhering conductive foil 350 to both the inside and outside surfaces of the coil form. This effectively provides two single layers of conductive foil 350 on opposing faces of the non-conductive form, which may have multiple benefits. First, the conductor cross section area is doubled, resulting in lower coil DC resistance and possible higher coil Q factor, with only a small increase in coil size and mass. Second, the capacitive spacing D can be formed with an all air, inert gas, or vacuum gap, making the dielectric dissipation factor low and the intrinsic capacitance of the coil very low and inherently temperature stable. This is beneficial in keeping the system tuned to a desired resonant frequency for maximum efficiency and power transfer. Conductive foil 350 may be adhered to the electrically non-conductive form with any suitable adhesive such as epoxy, urethane, silicone, or acrylic. In some implementations, conductive foil 350 may also extend over the edges of the coil form to make electrical contact between foil on the inside and outside surfaces of the coil. Alternately, if a coil form with circular cross section is used, conductive foil 350 may be wrapped around the entire circumference of the coil form to eliminate current concentrations at conductor edges.

Alternately, the conductive path of resonant coils 325 and 335 may be formed by electroplating or electroless plating of a conductive material such as copper or silver onto a suitable electrically non-conductive form. This may result in multiple advantages. First, manufacturing material and labor costs may be lower due to eliminating costs associated with adhering conductive foil to an electrically non-conductive form. Secondly, the conductive path formed by electroplating or electroless plating is continuous around the electrically non-conducting form which may further lower coil AC resistance and increase coil Q factor. The thickness of the conductive layer plated onto the electrically non-conductive form is chosen such that the skin depth ratio is less than 2 for a given operating frequency between 30 kHz-15 MHz. Again, this is done to minimize the proximity effect and lower coil AC resistance and increase coil Q factor. Electroless plating of conductive material onto an electrically non-conductive form may be preferred over electroplating to produce a more uniform conductor thickness throughout the coil geometry. The electrically non-conductive form may be made from a material that is readily platable with copper or silver such as ABS, nylon, or polycarbonate.

Another factor which determines how much power can be transferred between transmitting coil assembly 310 and receiving coil assembly 315 is the coupling coefficient between transmitting 325 and receiving 335 resonant coils. The coupling coefficient is a function of coil geometry and varies between 0 and 1. Higher coupling coefficients allow more power to be transferred between resonant coils across greater distances. Coil turns of transmitting 325 and receiving 335 resonant coils are spaced apart (distance D shown in FIG. 26a) by at least 0.003 inches, preferably 0.030 inches or greater, to increase the coupling coefficient between coils. This also has the added benefit of reducing resonant coil intrinsic capacitance.

An alternate conducting medium for resonant coils 325 and 335 for frequencies in the range 30 kHz-5 MHz is Litz wire, which is a type of cable designed to reduce the skin effect and proximity effect losses in conductors, thereby reducing the AC resistance. Litz wire consists of multiple conductors in the form of thin round wire strands, individually insulated and twisted or woven together, following one of several prescribed patterns intended to equalize the proportion of the overall length over which each strand is at the outside. Preferably, each strand has a skin depth ratio of approximately one or less for a given operating frequency between 30 kHz-5 MHz. Operation in lower frequency ranges, for example, 135 kHz, provides several advantages for use in medical implants, including, but not limited to, increased electromagnetic safety and improved performance in the presence of metallic shielding.

Because of the criticality of this wireless power system in life support applications, such as a VAD or TAH, fault-tolerance is desired. If a failure were to occur which impairs the power transfer using magnetic resonance coupling, the excitation coil 320 and power pick-up coil 340 could be used directly as power transfer coils utilizing traditional inductive coupling over a shorter distance. For example, transmitting coil assembly 310 may be placed on the patient's body near the location of receiving coil assembly 315. To minimize the inductive coupling distance and maximize the power transfer, in some implementations it may be desirable to orient the excitation coil 320 and the power pick-up coil 340 proximate to each other with their respective transmitting and receiving resonant coils 325 and 335 being oriented distally. In other implementations, a second excitation coil separate from the transmitting coil assembly may be used to supply power inductively to the power pick-up coil 340. A suitable frequency range of operation for this inductive backup mode is 30 kHz-1 MHz, with an exemplary value being 135 kHz. While this backup mode operation is suitable for all of the previously described implementations, it is especially well suited for the Litz wire resonant coil because both the magnetic resonance coupling and the backup inductive coupling may be operated at the same frequency, simplifying system design and reducing complexity. In an alternative fault-tolerance approach, the receiving resonant coil 335 may be removed from the receiving coil assembly 315 and used as an external (non-implantable) resonator when placed in proximity to the power pick-up coil 340 in the receiving coil assembly 315. The power pick-up coil may then be used for inductive coupling as well as for collecting power from the external receiving resonant coil when magnetic resonance coupling is available.

Figure 27:
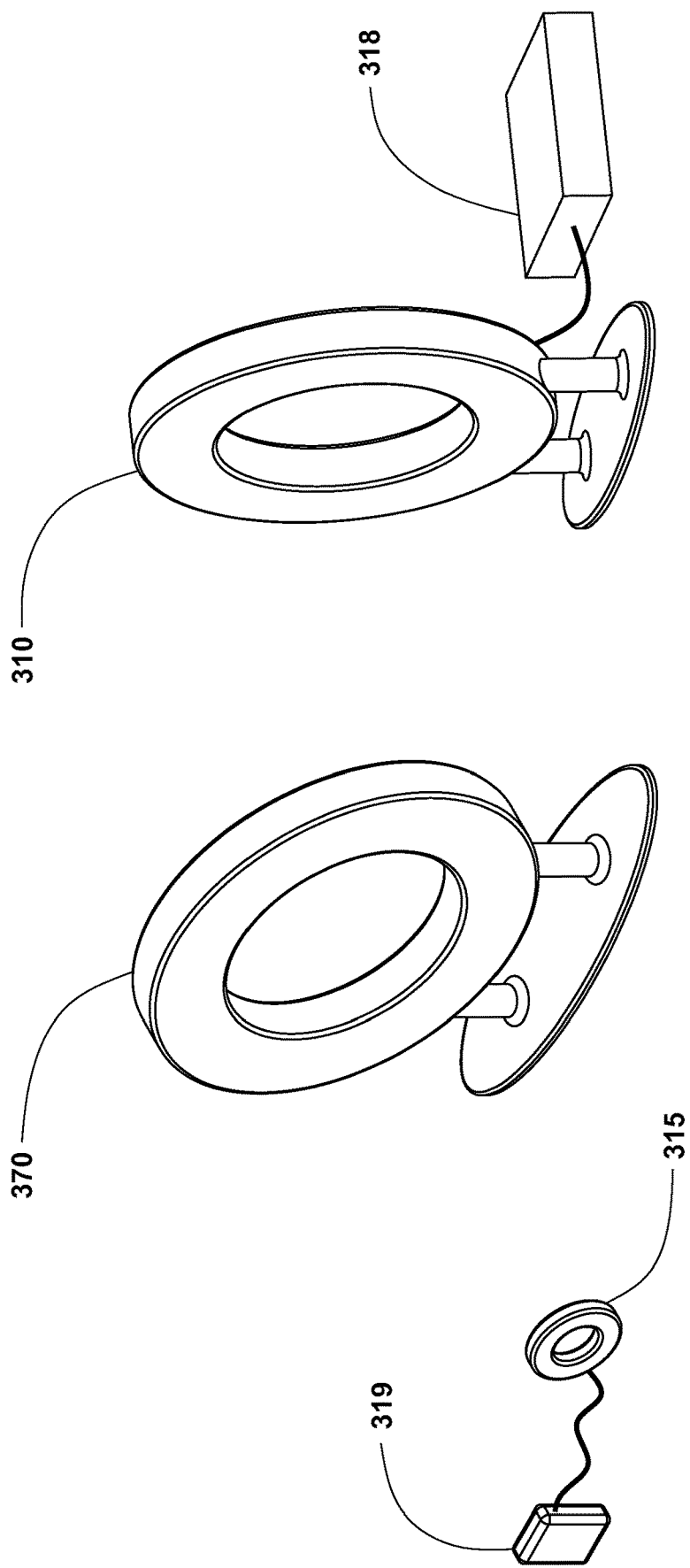
FIG. 27 is an illustrative implementation of a wireless power system with a sympathetic coil.

The power transfer efficiency of magnetic resonance coupling is increased when the Q factor of either or both of the resonant coils 325 and 335 is increased. Additional "sympathetic" resonant coils, meaning those which closely match or are identical to the resonant frequency of the transmitting and receiving resonant coils 325 and 335, may be used to increase the power transfer efficiency and range of the transmitting and receiving resonant coils 325 and 335. For example, one or more sympathetic resonant coils 370 may be placed near the transmitting resonant coil 325 to improve the power transfer efficiency as shown in FIG. 27. The additional coils may be placed in geometric positions that enhance the directionality or universality of the power transfer. For example, the additional coils may be placed at angle(s) relative to the transmitting resonant coil 325 that increase the spatial coverage of the implantable wireless power subsystem. In some implementations, additional coils may be placed near or around the receiving resonant coil 335. The sympathetic resonant coil 370 shown in FIG. 27 is illustrative only; sympathetic resonant coil 370 may be in any shape, form factor, or quantity necessary to enhance the efficiency or range of power transfer among the resonant coils 325, 335 and 370. Sympathetic resonant coil 370 should have a Q factor sufficiently high in order to provide reasonably efficient energy transfer. It may be advantageous to place one or more sympathetic resonant coils so that they, along with the transmitting resonant coil 325, are over-coupled. When a first resonant coil is placed within a critical coupling distance near another resonant coil, the resonant coils have a tendency to operate optimally at a shared resonant frequency different from their independent natural resonant frequency, which is described as over-coupled. In contrast, when a first resonant coil is substantially distant from another resonant coil, or outside of a critical coupling distance, the resonant coils maintain optimum operation at their respective natural resonant frequencies, which is described as under-coupled. In such a system, the transmitting resonant coil 325 and one or more sympathetic resonant coils 370 produce a magnetic resonance field which shares and stores energy. This use of sympathetic resonant coil 370 is different from a use which would transfer energy from transmitting resonant coil 325 to receiving resonant coil 335 via "repeating" or "bucket brigade" architecture wherein sympathetic resonant coil 370 is an intermediary. Instead, this over-coupled mode ensures that the sympathetic resonant coil 370 has a shared resonant frequency with transmitting resonant coil 325. When receiving resonant coil 335 is substantially distant from transmitting resonant coil 325 and sympathetic resonant coil 370, receiving resonant coil 335 may be under-coupled. Alternatively, as receiving resonant coil 335 moves substantially near either transmitting resonant coil 325 or sympathetic resonant coil 370, receiving resonant coil 335 may be over-coupled and produce a shared resonant frequency.

Figure 28:
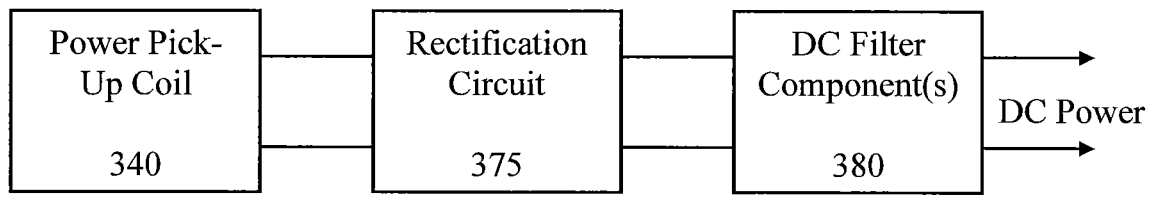
FIG. 28 is a functional block diagram of a rectifier and DC filter components connected to a power pick-up coil.

The hermetically-sealed biocompatible housing 345 and cover 346 are preferably composed of geometries and materials which do not adversely affect the Q factor of the receiving resonant coil 335 or the power transfer efficiency of the wireless power subsystem. Such materials may include, but are not limited to, polyetheretherketone (PEEK), polyetherimide (ULTEM), polysulfone (UDEL), polytetraflouroethylene (PTFE, Teflon), polyurethane (Tecothane), and silicone. Additionally, the geometries and materials are chosen to provide electrical insulation for the potential high voltages that may be generated in the receiving resonant coil 335, as well as provide spacing necessary to minimize adverse impacts on the quality factor Q of receiving resonant coil 335 due to extraneous materials. Environmental capacitance, meaning capacitance in the vicinity of transmitting resonant coil 325 or receiving resonant coil 335, adversely affects the resonant frequency of coil 325 or 335 and consequently must be minimized. Therefore, the hermetically-sealed biocompatible housing 345 and cover 346 provide spacing around coil 335 and a stable electrostatic environment intended to stabilize environmental capacitance. In this way, the hermetically-sealed biocompatible housing 345 and cover 346 minimize detuning and Q factor reduction which would otherwise occur were housing 345 and cover 346 not designed specifically for that advantage. Sealing of biocompatible housing 345 may be accomplished with an enclosed housing or potting of an open housing using any suitable potting compound. In other implementations, sealing may be accomplished by potting the entire assembly of receiving coil assembly 315. While the hermetically-sealed biocompatible housing 345 is shown without other electronics or mechanical components common to active implantable medical devices, such as batteries, power rectification and conditioning circuitry, connectors and the like, such components may be included in or attached to housing 345. In some implementations, such components may be housed in a separate biocompatible housing. In other implementations, it may be advantageous to perform AC/DC rectification and some or all DC filtering within receiving coil assembly 315 to reduce high frequency losses which may occur in the implantable biocompatible cable connecting receiving coil assembly 315 to the power module 319. In such cases the rectifier 375 may be placed adjacent to or inside power pick-up coil 340 as shown functionally in FIG. 28. Similarly, some or all DC filter components 380, such as capacitors and inductors for a π type filter, may be placed adjacent to or inside power pick-up coil 340 also shown functionally in FIG. 28. One advantage of this approach is that the intrinsic capacitance and inductance of the implantable biocompatible cable connecting receiving coil assembly 315 and power module 319 may be leveraged as part of a π filter. All electronic components for the wireless power subsystem can be selected for high reliability. High reliability is especially desirable for components that are to be implanted in a patient to avoid surgery to remove or repair the system. Likewise, all components of the subsystem may be selected for compatibility with the electromagnetic fields which will be produced during the energy transfer.

The resonant coils 325 and 335 implementation previously described is a right circular spiral coil, where the start and end of the coil conductor is within 45 degrees of each other in order to reduce the effective antenna dipole and reduce electromagnetic radiation. In other implementations, any suitable coil arrangement may be utilized, such as a rectangular coil, a helical coil, a square coil, or any other suitable structure. The number of turns may be one or more. The coil may be composed of a solid conductor, hollow conductor, flat conductor, Litz wire, any other suitable conductors, and/or a combination thereof. All manner of coil shapes, including, but not limited to, circles, squares, rectangles, octagons, other polygons, regular areas and irregular areas, are within the scope of this invention. While the illustrative implementations utilize copper or silver conductor coils, any suitable conductive materials or combination of conductive materials may be utilized.

Cardiac Support System

Figure 29:
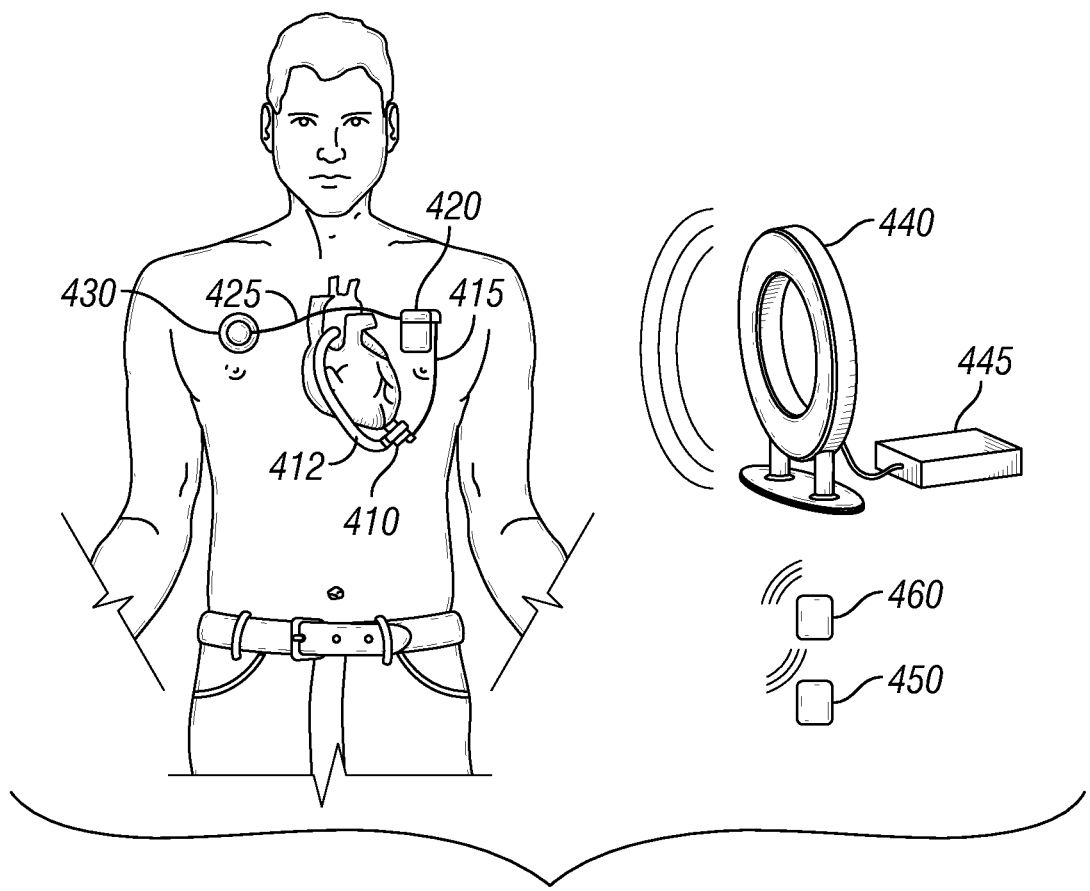
FIG. 29 is an illustrative implementation of anatomical positioning of components of a cardiac support system.

FIG. 29 is an illustrative implementation of a cardiac support system, which may include an implantable rotary blood pump, an implantable power module, a wireless power transfer subsystem, a patient monitor, and a programmer. The illustrative implementation shown provides blood pump 410, outflow graft 412, pump cable 415, power module 420, receiver cable 425, receiving coil assembly 430, transmitting coil assembly 440, radio frequency (RF) power supply 445, patient monitor 450, and programmer 460. Blood pump 410 has a fluid inlet and a fluid outlet connected to an impeller chamber, within which an impeller resides. The impeller is fashioned so that when it is rotated by a force external to the impeller, it will impart motive energy to a fluid in the impeller chamber to increase flow of that fluid from the inlet to the outlet. When applied to the cardiac circulatory system, the increased flow may be used for therapeutic purposes such as, but not limited to, ventricular assist (right, left and both) and heart replacement.

Blood pump 410 inlet is preferably attached to the left ventricular apex of the heart directly or via cannula (not shown) and the outlet is preferably attached to the aorta via outflow graft 412. The impeller chamber is composed of a biocompatible material, such as titanium or any other suitable material. The impeller chamber further is fashioned to minimize adverse impact to the blood which flows through the impeller chamber.

Blood pump 410 impeller is configured to rotate and impart force on blood moving from the inlet and delivering blood to the outlet. To induce blood flow, as with any fluid, power must be imparted to the fluid. The hydraulic power necessary to produce fluid flow is:

$$W_{flow} = \frac{flow \times density \times \Delta P \times g}{6 \times 10^7} \quad [4]$$

where $W_{flow}$ is in watts, flow is the desired fluid flow rate in liters per minute (LPM), density is the fluid density in kg/m³, ΔP is the differential pressure between inlet and outlet in vertical column mm, and g is the acceleration of gravity in m/s². The cardiac support system minimizes power losses while providing the power necessary for the intended blood flow in order to provide an energy-efficient system suitable for an unencumbered daily lifestyle. The power necessary to rotate an impeller is:

$$W_{impellar} = \frac{torque \times 2\pi \times speed}{60} \quad [5]$$

where $W_{impeller}$ is in watts, torque is the turning force of the impeller in Newton-meters, and speed is the impeller rotational rate in rotations per minute (RPM). The power efficiency of a pump can be defined as:

$$\eta_{pump} = \frac{W_{flow}}{W_{impeller}} \quad [6]$$

Blood pump 410 impeller is rotated by a motor, which is magnetically coupled to the impeller. A significant advantage of the magnetic coupling is that the motor chamber and the impeller chamber remain isolated, thereby avoiding blood damage from the motor and coupling between the motor and the impeller. When the chambers are not separated, the motor must be suitable for operating in blood. In other blood pumps, the motor is mechanically coupled to an impeller in a separate chamber through seals or the like to separate the blood from the motor. However, the mechanical coupling and seals may result in blood clots, and blood may enter the motor if the seals fail. The efficiency of a motor which converts electrical power into mechanical rotational power can be defined as:

$$\eta_{motor} = \frac{W_{impeller}}{W_{motor}} \quad [7]$$

where $W_{motor}$ is the motor input electrical power in watts, which is proportional to the product of motor input voltage in volts ($V_{motor}$) and motor input current in amps ($I_{motor}$). The typical maximum motor efficiency is:

$$\eta_{motorMax} = \left(1 - \sqrt{\frac{I_0}{I_A}}\right)^2 \quad [8]$$

where $I_0$ is the no-load motor current in amps and $I_A$ is the motor stall current in amps. The maximum motor efficiency is reached when:

$$I_{motor} = \sqrt{I_0 \times I_A} \quad [9]$$

The cardiac support system maximizes motor efficiency by minimizing $I_0$ and maximizing $I_A$. To minimize $I_0$, motor frictional losses are minimized by utilizing low-loss internal bearings. Blood pump 410 may utilize any suitable motor, such as a brushless DC (BLDC) motor to eliminate frictional losses of brushes and increase reliability. To maximize $I_A$, motor windings are designed using low-loss conductors, frame materials, geometries to reduce winding losses, and small air gaps to minimize flux losses. During operation, when motor speed adjustment is needed, this invention may adjust the speed by adjusting $V_{motor}$ (wherein speed is proportional to $V_{motor}$) while simultaneously maintaining maximum motor efficiency by specifically operating the motor at or near $I_{motor}$ equal to the value given in equation 9.

The electrical power and control signals are delivered to the blood pump 410 through pump cable 415. Pump cable 415 may connect to blood pump 410 and power module 420 using connectors on one or both ends suitable for implanted medical devices.

By utilizing a power-efficient blood pump 410, the cardiac support system minimizes the amount of power required to operate the system. Note that the cardiac support system utilizes a magnetically coupled motor and impeller that are provided in separate chambers. Some blood pumps have attempted to reduce pump size by integrating the impeller into the motor as the rotor itself. This approach may reduce pump size, but because of design constraints, both the impeller and motor are difficult to optimize for power efficiency. This approach may result in an impeller with suboptimal efficiency, a motor with suboptimal efficiency, or both. In contrast, a magnetically coupled motor and impeller allows a highly efficient motor to be utilized without affecting the efficiency of the impeller design. Surprisingly, this magnetic coupling approach does not result in a pump significantly larger than other LVADs. More importantly, the highly efficient blood pump 410 allows energy storage needed to power the pump for a full day of awake hours to be implanted in a patient. While the LionHeart LVD-2000 uses an implanted rechargeable energy source in the patient, the rechargeable energy source is only capable of providing short duration operation. Blood pump 410 is capable of operating for an entire day of awake hours on power provided by an implanted rechargeable energy source.

Blood pump 410 is small enough for implantation above the diaphragm or pericardially. Power module 420 is separated from blood pump 410 so that power module 420 may be implanted outside of the pericardium. For example, power module 420 may be implanted subcutaneously in the pectoral region near the clavicle, such as done with implantable pacemakers and defibrillators. The separated implant location of power module 420 is advantageous should the module need to be replaced, in which case only subcutaneous outpatient surgery would be needed instead of surgery requiring pericardial intrusion. Because of the cardiac support system energy efficiency, power module 420 volume may be approximately 150 cc or less, which is small enough for implantation above the diaphragm or pectorally. Pump cable 415 connects power module 420 to blood pump 410, which allows power module 420 to power and control blood pump 410. Pump cable 415 may utilize multi-filar MP-35N wire, or other biocompatible metals or alloys, fabricated to provide high reliability and long-term durability. The conductors may be electrically insulated from each other and from the tissue surrounding the implanted pump cable 415 utilizing flexible biocompatible materials, such as silicone, Silastic, and/or any suitable material(s).

Power module 420 is contained in a housing composed of a biocompatible material. The housing provides a hermetic seal for the components of power module 420. However, it is recognized by one of ordinary skill in the art that various components of power module 420 may be provided in separate housings and/or incorporated with other components of the cardiac support system.

Receiving coil assembly 430 may be connected to power module 420 by receiving cable 425. Receiving coil assembly 430 may be approximately 100 cc or less in volume, and is small enough for implantation above the diaphragm or pectorally. Transmitting coil assembly 440 is capable of transferring electromagnetic energy to receiving coil assembly 430 through the patient's body. Transmitting coil assembly 440 and receiving coil assembly 430 are utilized to power blood pump 410, provide energy to be stored by a rechargeable energy source powering blood pump 410, or both. Receiving coil assembly 430 and transmitting coil assembly 440 are capable of magnetic resonance coupling (MRC), which provides a significantly greater electromagnetic recharging distance than inductive coupling. Receiving coil assembly 430 may be operated in either MRC or inductive coupling modes, the latter requiring a shorter electromagnetic recharging distance. Monitor 450 may be utilized to monitor blood pump 410 and may transmit/receive data via RF or LF electromagnetic coupling. Programmer 460 may be utilized to operate/control blood pump 410 and may transmit/receive data via RF or LF electromagnetic coupling. In some implementations, monitor 450 and programmer 460 may be combined into a single device.

Figure 30:
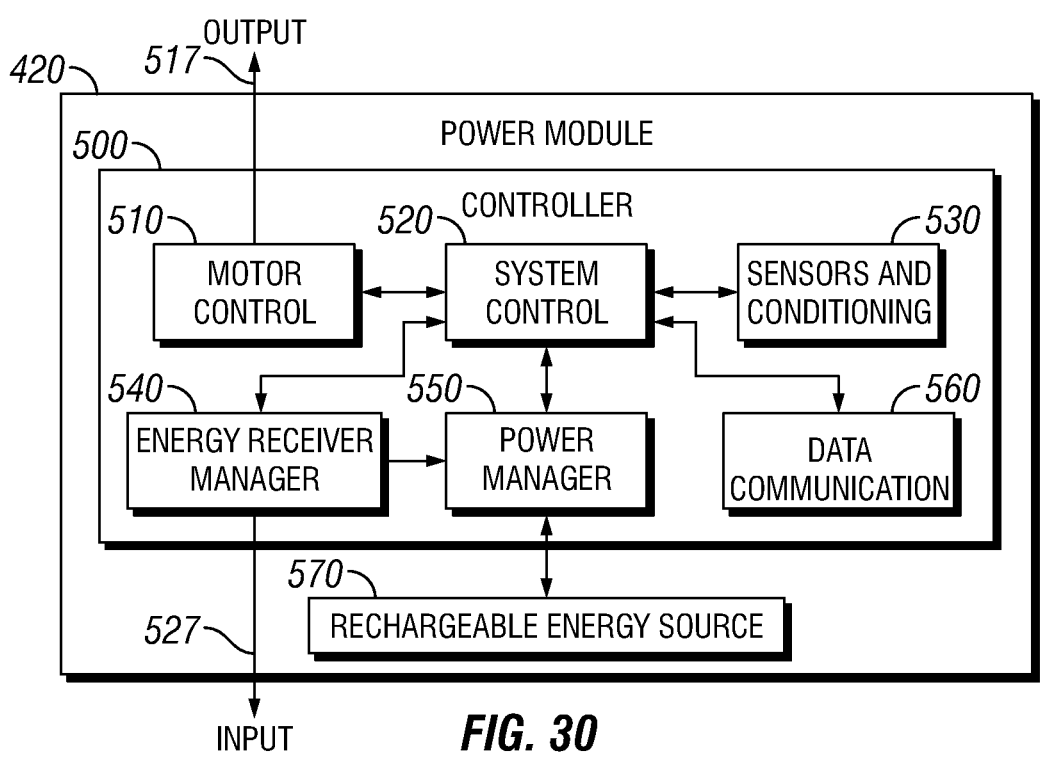
FIG. 30 is a block diagram of an implantable power module.

FIG. 30 is an illustrative implementation of power module 420. Power module 420 may include an output 517, an input 527, controller 500, motor control 510, system control 520, sensors and conditioning 530, energy receiver manager 540, power manager 550, data communication 560, and rechargeable energy source 570. Rechargeable energy source 570 provides the energy necessary to operate blood pump 410 as well as implantable controller 500. Rechargeable energy source 570 may be a high energy density rechargeable battery based upon lithium chemistry, such as Li-ion. However, any suitable energy storage mechanism may be used as rechargeable energy source 570, such as non-chemical rechargeable energy storage devices such as high energy capacitors. Further, battery cell(s) or capacitor(s) may be used in combination. An exemplary energy density for rechargeable batteries is at least 150 watt-hours/liter, with Li-ion batteries exceeding 250 watt-hours/liter. Depending upon the energy capacity needed, rechargeable energy source 570 may be the largest implantable component in volume. By utilizing high energy density rechargeable energy source 570, power module 420 is capable of powering blood pump 410 for a full day of awake hours, while still remaining a size suitable for pectoral implantation.

Power module 420 also contains the electronics provided by controller 500. These electronics may be fabricated of one or more integrated circuits and passive electronic components. Controller 500 may provide reprogrammable/reconfigurable software, firmware, and/or hardware.

Power module 420 receives power and/or control signals from input 527, which are routed to motor control 510. Motor control 510 operates the motor in blood pump 410 at the peak efficiency described previously. Motor control 510 may use pulse width modulation (PWM) of a DC power signal to control the speed of blood pump 410. Motor control 410 may use power transistors (e.g. MOSFETs) to perform the PWM switching, wherein the power transistors are designed to minimize switching losses. The PWM frequency may be selected with consideration of inductances and capacitances in pump cable 415 and blood pump 410 to reduce power losses due to reactive mismatches.

One function of power manager 550 is to provide power as needed to the functional blocks shown in controller 500. For example, motor control 510 may receive power from the rechargeable energy source 570 or energy receiver manager 540 via power manager 550. Power manager 550 may condition or modify power characteristics, such as voltage. However, to maximize efficiency, power manager 550 may route power with little or no conversion to minimize conversion losses as appropriate. Motor control 510 may contain sufficient switching logic to efficiently maintain the speed of blood pump 410 as long as the voltage provided to motor control 510 is between 8 to 20 volts. Power manager 550 may then route power from energy receiver manager 540 or rechargeable energy source 570 to blood pump 410, while either of their available voltages is between 8 to 20 volts. Alternatively, power manager 550 may convert an available voltage to a desired range when it is outside of the desired range. In some implementations, power manager 550 may utilize fixed high efficiency conversion circuitry to supply ultra-low-wattage power for other circuitry in controller 500.

Motor control 510 may receive control information from system control 520 and return operational status, such as drive currents and speed information. Motor control 510 may be in power module 420. However, in other implementations, motor control 510 may be placed in blood pump 410. The motor, which may be a BLDC motor, may be a multi-phase motor requiring commutation of the signals delivered to each phase. In such implementations, motor control 510 may provide the electrical commutation, examples of which are trapezoidal or vector-sinusoidal. The combined power efficiency of motor control 510 and power manager 550 can be defined as:

$$\eta_{control} = \frac{W_{motor}}{W_{eSource}} \quad [10]$$

where $W_{eSource}$ is the power from the rechargeable energy source 570 used by motor control 510 and power manager 550 to produce $W_{motor}$.

Controller 500 may also include energy receiver manager 540, which is electrically and operationally connected to receiving coil assembly 430 via receiver cable 425. Energy transferred to receiving coil assembly 430 by magnetic resonance coupling or inductive coupling is provided to energy receiver manager 540 for storage and/or to power blood pump 410. Energy receiver manager 540 may additionally include power conditioning and protection circuitry appropriate for receiving coil assembly 430 to maximize electromagnetic energy transfer and transfer distance. In some implementations, receiving coil assembly 430 may be incorporated into power module 420, eliminating receiver cable 425 and reducing the number of components that are implanted.

Power manager 550 efficiently provides power to the other components of power module 420 and receives that power from rechargeable energy source 570 and/or energy receiver manager 540. Power manager 550 is also responsible for recharging rechargeable energy source 570 using power from energy receiver manager 540. While energy receiver manager 540 is intended primarily for recharging rechargeable energy source 570 through power manager 550, it may also be used for continuous power delivery to blood pump 410 from motor control 510 through power manager 550. Rechargeable energy source 570 acts primarily as an energy storage and source for periods when energy receiver manager 540 is not receiving sufficient power to power blood pump 410 through motor control 510.

Power manager 550 is responsible for all power conditioning, including DC-DC conversion, current limiting, over-power protection, and/or management of rechargeable energy source 570. Management of rechargeable energy source 570 may include management of one or more battery cells and charge/discharge operations suitable for long-term preservation and management of the battery cells. Power manager 550 may provide efficient energy delivery or conversion from rechargeable energy source 570 to various components of power module 420 and may deliver energy to motor control 510 to maximize $\eta_{control}$. Regarding management of battery cells, power manager 550 may also contain logic for constant-current and constant-voltage delivery for Li-ion cell recharging.

To send and receive data transcutaneously, controller 500 includes a power-efficient data communication 560 for wireless data transfer utilizing radio frequency (RF) communication or the like. Data communication 560 performs data formatting, error checking, modulation, transmission and reception of data. For example, data communication 560 may utilize the industry-standard MICS band for communication. In other implementations, data communication 560 may utilize low frequency (LF) inductively-coupled communication. Data sent to or received from non-implanted devices may be communicated to or from system control 520 or other components of power module 420 as appropriate. Data may be sent by data communication 560 to patient monitor 450 via RF or LF electromagnetic coupling so that patient monitor 450 may receive information, such as but not limited to, pump or battery status, and present that information to the patient or caregiver using one or more indicators on or associated with patient monitor 450. The indicators may include, but are not limited to, visual, auditory and tactile indicators, with respective examples being lights, beeps and vibrations. Additionally, data may be sent to data communication 560 from programmer 460 via RF or LF electromagnetic coupling so that programmer 460 may send information, such as but not limited to, new pump speed, for use by implantable controller 500. Through this interface, operational parameters may be adjusted by a health care professional or, depending upon the criticality of the parameter, the patient or caregiver. Operational parameter(s) may be used by controller 500 to alter operational behavior of blood pump 410, controller 500 itself, rechargeable energy source 570, and/or receiving coil 430.

Power module 420 may optionally include sensors and conditioning 530 to sense, amplify, filter and condition as needed one or more parameters for utilization by controller 500 for monitoring, recording and/or altering the operation of the controller 500 or blood pump 410. For example, an accelerometer and appropriate circuitry within sensors and conditioning 530 may be provided to detect acceleration as an indication of increased physical activity. The accelerometer sensor may act as a physiological demand sensor, in response to which controller 500 may increase or decrease the speed of blood pump 410 to meet the patient's physiologic needs. In some implementations, sensors and conditioning 530 may monitor a voltage differential between points which are electrically connected to the housings of power module 420 and blood pump 410, providing an intrinsic cardiac activity sensor. Sensors and conditioning 530 then may filter and amplify the cardiac activity signal and controller 500 may then use the intrinsic cardiac activity to increase or decrease the speed of blood pump 410 to meet the patient's needs. There may be therapeutic advantages to varying the pump speed cyclically to produce pulsed blood flow which mimics normal heart operation. Because of the efficiency of blood pump 410, less motor torque is needed to produce a particular flow rate than other pumps. Thus, blood pump 410 is suitable for efficiently producing a pulsed blood flow if desired. Furthermore, the pulse rate range may cover the entire physiologically observed range of 20 to 220 pulses per minute. When blood pump 410 is used in conjunction with controller 500 containing sensors and conditioning 530, the pulsed blood flow may be adjusted dynamically in response to the previously described sensors for cardiac activity, physiological demand, or both. Such physiologic flow adaptability may be advantageous because it facilitates an increased ambulatory and active lifestyle. Sensors and conditioning 530 may contain the physiologic or environmental sensors themselves; alternatively, the sensors may be located outside sensors and conditioning 530, outside controller 500, or outside power module 420 and located as needed.

System control 520 performs supervisory and data exchange functions. System control 520 may include a microprocessor, microcontroller, or reconfigurable hardware core, whether implemented discretely or within a multi-function integrated circuit. In addition to the power utilized by blood pump 410, components of power module 420 consume a small, but finite, amount of power independent of the blood flow rate. The average amount of such power consumed by power module 420 is defined as $W_{baseline}$, and the components of power module 420 are designed to minimize this value. For example, power module 420 may include low-voltage, low-switching-speed CMOS circuitry and idle power-down techniques between time-critical operations. Wherever applicable, circuits which consume power during state transitions are operated to minimize state transitions, and circuits which consume power during stasis are powered down whenever possible.

The cardiac support system implements an energy-efficient system having a rechargeable energy source 570 capacity requirement of:

$$\text{Energy} = \left( \frac{W_{flow}}{\eta_{pump} \times \eta_{motor} \times \eta_{control}} + W_{baseline} \right) \times T \quad [11]$$

where Energy is in Watt-hours and T is the period of time in hours that rechargeable energy source 570 is to provide the desired flow. The cardiac support system, by maximizing the component η efficiencies (each of which will be 1 or less) and minimizing $W_{baseline}$, results in a reduced-size implantable system capable of providing a desired flow for a desired period of time between recharges. By maximizing and combining the component η efficiencies, the cardiac support system has achieved a $\eta_{pump} \times \eta_{motor} \times \eta_{control}$ value of approximately 0.6. Similarly, this invention has minimized $W_{baseline}$ to a comparatively negligible level. In contrast, other systems such as those described previously have equivalent $\eta_{pump} \times \eta_{motor} \times \eta_{control}$ values less than 0.1.

In order to quantify performance relative to the amount of power consumed, an analogous and proportionate summary value for energy efficiency may be defined wherein the rechargeable energy source and all but one energy output variables are set to clinically relevant standard values. An Energy Conversion Ratio (ECR) may be defined as:

ECR=the sustained flow rate (in LPM) a cardiac support system can provide against 100 mm-Hg differential pressure for 24 hours from a 40 Watt-hour rechargeable energy source To further standardize ECR, a blood hematocrit value of 42% is used, which is the average between male and female patients. Other cardiac support systems such as those described previously have ECR values below 0.8. The cardiac support system as described herein is capable of producing blood flow with an ECR of approximately 4.0.

The invention is not limited to the preferred implementations, but instead these and other variations of construction are obvious to those skilled in the art and are understood to be within the scope and spirit of the invention herein described.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

What is claimed is the following:

1. A method for treating heart failure, the method comprising:
    generating an amount of blood flow with a rotary blood pump implanted in a patient;
    coupling a transmitting coil assembly to a receiving coil assembly, implanted in the patient and contained within an implantable housing, using magnetic resonance coupling, such that the transmitting coil assembly electromagnetically transfers energy to the receiving coil assembly; and
    storing, in a power module implanted in the patient and contained within the implantable housing, the energy transferred to the receiving coil assembly, the energy being utilized to operate the rotary blood pump.

2. The method of claim 1, wherein the receiving coil assembly comprises a receiving resonant coil having a quality factor above 300.

3. The method of claim 1, wherein the transmitting coil assembly comprises a transmitting resonant coil having a quality factor above 600.

4. The method of claim 1, wherein the amount of blood flow is generated with an ECR of 1.0 or greater using the energy stored in the power module.

5. The method of claim 1, wherein the amount of blood flow is generated with an ECR of 2.5 or greater using the energy stored in the power module.

6. The method of claim 1, wherein the amount of blood flow is generated with an ECR of 4.0 or greater using the energy stored in the power module.

7. The method of claim 1, wherein the receiving coil assembly is 100 cc or less in volume.

8. The method of claim 1, wherein the power module is 150 cc or less in volume.

9. The method of claim 1, further comprising detecting cardiac activity, wherein the amount of blood flow is adjusted in accordance with the cardiac activity detected.

10. The method of claim 1, further comprising detecting physiological demand, wherein the amount of blood flow is adjusted in accordance with the physiological demand detected.

11. The method of claim 1, further comprising monitoring the rotary blood pump wirelessly, wherein status information is provided visually, acoustically, or tactilely.

12. The method of claim 1, wherein the amount of blood flow generated is pulsatile.

13. The method of claim 1, further comprising programming the rotary blood pump wirelessly, wherein programming data is provided via RF or low frequency electromagnetic coupling.

14. The method of claim 13, wherein the programming data alters an operational setting of the rotary blood pump, power module, or receiving coil assembly.

* * * * *